United States Patent
Devens, Jr.

(10) Patent No.: US 7,815,628 B2
(45) Date of Patent: *Oct. 19, 2010

(54) MULTILAYER MEDICAL DEVICES

(75) Inventor: Douglas A. Devens, Jr., St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/346,597

(22) Filed: Dec. 30, 2008

(65) Prior Publication Data

US 2009/0125000 A1    May 14, 2009

Related U.S. Application Data

(63) Continuation of application No. 11/640,093, filed on Dec. 15, 2006, now Pat. No. 7,481,804, which is a continuation of application No. 10/645,014, filed on Aug. 21, 2003, now Pat. No. 7,166,099.

(51) Int. Cl.
*A61M 25/00* (2006.01)

(52) U.S. Cl. .................................... 604/525

(58) Field of Classification Search ......... 604/523, 604/524, 525, 526, 527, 530, 532, 533, 534, 604/535, 264, 265
See application file for complete search history.

(56) References Cited

U.S. PATENT DOCUMENTS

| | | | |
|---|---|---|---|
| 3,733,309 A | 5/1973 | Wyeth et al. |
| 3,745,150 A | 7/1973 | Corsover |
| 3,752,617 A | 8/1973 | Burlis et al. |
| 3,769,984 A | 11/1973 | Muench |
| 3,771,527 A | 11/1973 | Ruisi |
| 3,799,172 A | 3/1974 | Szpur |
| 3,807,408 A | 4/1974 | Summers |
| 3,814,137 A | 6/1974 | Martinez |
| 3,833,004 A | 9/1974 | Vazquez et al. |
| 3,837,347 A | 9/1974 | Tower |
| 3,861,972 A | 1/1975 | Glover et al. |
| 3,889,685 A | 6/1975 | Miller, Jr. et al. |
| 3,924,634 A | 12/1975 | Taylor et al. |
| 3,959,426 A | 5/1976 | Seefluth |
| 3,962,519 A | 6/1976 | Rusch et al. |

(Continued)

FOREIGN PATENT DOCUMENTS

| CA | 2347024 A1 | 11/1995 |
|---|---|---|
| EP | 0729766 | 9/1996 |
| EP | 0987043 | 3/2000 |

(Continued)

OTHER PUBLICATIONS

Flash PTCA Balloon, 2 pages Posted on www.boltonmedical.com prior to filing date of U.S. Appl. No. 10/787,777, filed Feb. 26, 2004.
List of References [online], 7 pages Retrieved from the Thomson Derwent World Patent Index.

*Primary Examiner*—Manuel A Mendez
(74) *Attorney, Agent, or Firm*—Crompton, Seager & Tufte, LLC

(57) ABSTRACT

A medical device includes at least four layers including a first material and a second material having a different stiffness than a stiffness of the first material, wherein at least one of the layers varies in thickness axially along the device.

20 Claims, 22 Drawing Sheets

U.S. PATENT DOCUMENTS

| | | |
|---|---|---|
| 3,996,938 A | 12/1976 | Clark, III |
| 4,035,534 A | 7/1977 | Nyberg |
| 4,047,868 A | 9/1977 | Kudo et al. |
| 4,061,707 A | 12/1977 | Nohtomi et al. |
| 4,079,850 A | 3/1978 | Suzuki et al. |
| 4,085,757 A | 4/1978 | Pevsner |
| 4,105,022 A | 8/1978 | Antoshkiw et al. |
| 4,140,126 A | 2/1979 | Choudhury |
| 4,141,364 A | 2/1979 | Schultze |
| 4,195,637 A | 4/1980 | Gruntzig et al. |
| 4,198,981 A | 4/1980 | Sinnreich |
| 4,213,461 A | 7/1980 | Pevsner |
| 4,222,384 A | 9/1980 | Birtwell |
| 4,233,022 A | 11/1980 | Brady et al. |
| 4,250,072 A | 2/1981 | Flynn |
| 4,283,447 A | 8/1981 | Flynn |
| 4,581,390 A | 4/1986 | Flynn |
| 4,597,755 A | 7/1986 | Samson et al. |
| 4,627,436 A | 12/1986 | Leckrone |
| 4,627,844 A | 12/1986 | Schmitt |
| 4,636,346 A | 1/1987 | Gold et al. |
| 4,637,396 A | 1/1987 | Cook |
| 4,643,926 A | 2/1987 | Mueller |
| 4,782,834 A | 11/1988 | Maguire et al. |
| 4,790,831 A | 12/1988 | Skribiski |
| 5,047,045 A | 9/1991 | Arney et al. |
| 5,085,649 A | 2/1992 | Flynn |
| 5,094,799 A | 3/1992 | Takashige et al. |
| 5,100,381 A | 3/1992 | Burns |
| 5,100,721 A | 3/1992 | Akao |
| 5,100,992 A | 3/1992 | Cohn et al. |
| 5,102,416 A | 4/1992 | Rock |
| 5,108,415 A | 4/1992 | Pinchuk et al. |
| 5,108,420 A | 4/1992 | Marks |
| 5,114,423 A | 5/1992 | Kasprzyk et al. |
| 5,116,318 A | 5/1992 | Hillstead |
| 5,125,913 A | 6/1992 | Quackenbush |
| 5,137,512 A | 8/1992 | Burns et al. |
| 5,147,302 A | 9/1992 | Euteneuer et al. |
| 5,156,857 A | 10/1992 | Wang et al. |
| 5,160,321 A | 11/1992 | Sahota |
| 5,163,949 A | 11/1992 | Bonutti |
| 5,171,221 A | 12/1992 | Samson |
| 5,176,697 A | 1/1993 | Hasson |
| 5,179,174 A | 1/1993 | Elton |
| 5,183,613 A | 2/1993 | Edwards |
| 5,195,969 A | 3/1993 | Wang et al. |
| 5,195,970 A | 3/1993 | Gahara |
| 5,195,972 A | 3/1993 | Inoue |
| 5,201,706 A | 4/1993 | Noguchi et al. |
| 5,209,728 A | 5/1993 | Kraus et al. |
| 5,223,205 A | 6/1993 | Jackowski et al. |
| 5,226,880 A | 7/1993 | Martin |
| 5,248,305 A | 9/1993 | Zdrahala |
| 5,254,090 A | 10/1993 | Lombardi et al. |
| 5,254,091 A | 10/1993 | Aliahmad et al. |
| 5,263,962 A | 11/1993 | Johnson et al. |
| 5,270,086 A | 12/1993 | Hamlin |
| 5,272,012 A | 12/1993 | Opolski |
| 5,277,199 A | 1/1994 | DuBois et al. |
| 5,279,560 A | 1/1994 | Morrill et al. |
| 5,279,594 A | 1/1994 | Jackson |
| 5,290,306 A | 3/1994 | Trotta et al. |
| 5,304,171 A | 4/1994 | Gregory et al. |
| 5,304,197 A | 4/1994 | Pinchuk et al. |
| 5,306,246 A | 4/1994 | Sahatjian et al. |
| 5,312,356 A | 5/1994 | Engelson et al. |
| 5,318,041 A | 6/1994 | DuBois et al. |
| 5,318,587 A | 6/1994 | Davey |
| 5,330,428 A | 7/1994 | Wang et al. |
| 5,330,429 A | 7/1994 | Noguchi et al. |
| 5,334,146 A | 8/1994 | Ozasa |
| 5,342,307 A | 8/1994 | Euteneuer et al. |
| 5,344,401 A | 9/1994 | Radisch et al. |
| 5,358,486 A | 10/1994 | Saab |
| 5,364,357 A | 11/1994 | Aase |
| 5,366,472 A | 11/1994 | Hillstead |
| 5,372,603 A | 12/1994 | Acker et al. |
| 5,413,559 A | 5/1995 | Sirhan et al. |
| 5,441,484 A | 8/1995 | Atkinson et al. |
| 5,480,383 A | 1/1996 | Bagaoisan et al. |
| 5,499,973 A | 3/1996 | Saab |
| 5,499,980 A | 3/1996 | Euteneuer |
| 5,507,995 A | 4/1996 | Schweich, Jr. et al. |
| 5,509,899 A | 4/1996 | Fan et al. |
| 5,533,985 A | 7/1996 | Wang |
| 5,562,127 A | 10/1996 | Fanselow et al. |
| 5,658,263 A | 8/1997 | Dang et al. |
| 5,676,659 A | 10/1997 | McGurk |
| 5,728,063 A | 3/1998 | Preissman et al. |
| 5,730,733 A | 3/1998 | Mortier et al. |
| 5,755,690 A | 5/1998 | Saab |
| 5,759,173 A | 6/1998 | Preissman et al. |
| 5,759,191 A | 6/1998 | Barbere |
| 5,797,877 A | 8/1998 | Hamilton et al. |
| 5,820,594 A | 10/1998 | Fontirroche et al. |
| 5,824,173 A | 10/1998 | Fontirroche et al. |
| 5,843,032 A | 12/1998 | Kastenhofer |
| 5,851,203 A | 12/1998 | van Muiden |
| 5,868,704 A | 2/1999 | Campbell et al. |
| 5,951,494 A | 9/1999 | Wang et al. |
| 5,961,765 A | 10/1999 | Kastenhofer |
| 6,004,289 A | 12/1999 | Saab |
| 6,010,521 A | 1/2000 | Lee et al. |
| 6,027,477 A | 2/2000 | Kastenhofer |
| 6,030,369 A | 2/2000 | Engelson et al. |
| 6,045,547 A | 4/2000 | Ren et al. |
| 6,059,751 A | 5/2000 | Ostapchenko et al. |
| 6,086,556 A | 7/2000 | Hamilton et al. |
| 6,132,824 A | 10/2000 | Hamlin |
| 6,136,258 A | 10/2000 | Wang et al. |
| 6,165,166 A | 12/2000 | Samuelson et al. |
| 6,179,856 B1 | 1/2001 | Barbere |
| 6,195,969 B1 | 3/2001 | Yilmaz |
| 6,200,290 B1 | 3/2001 | Burgmeier |
| 6,299,596 B1 | 10/2001 | Ding |
| 6,319,228 B1 | 11/2001 | Kastenhofer |
| 6,406,457 B1 | 6/2002 | Wang et al. |
| 6,464,683 B1 | 10/2002 | Samuelson et al. |
| 6,465,067 B1 | 10/2002 | Wang et al. |
| 6,471,673 B1 | 10/2002 | Kastenhofer |
| 6,482,348 B1 | 11/2002 | Wang et al. |
| 6,488,655 B1 | 12/2002 | Wantink et al. |
| 6,589,226 B1 | 7/2003 | Owens |
| 6,776,945 B2 | 8/2004 | Chin et al. |
| 7,166,099 B2 * | 1/2007 | Devens, Jr. ................. 604/525 |
| 2002/0022824 A1 | 2/2002 | Kastenhofer |
| 2002/0081406 A1 | 6/2002 | Wang et al. |
| 2002/0165523 A1 | 11/2002 | Chin et al. |
| 2003/0009129 A1 | 1/2003 | Miller et al. |
| 2003/0088265 A1 | 5/2003 | Kastenhofer |
| 2003/0105426 A1 | 6/2003 | Jorgensen |
| 2003/0138582 A1 | 7/2003 | Miller et al. |

FOREIGN PATENT DOCUMENTS

| | | |
|---|---|---|
| EP | 1656174 | 5/2006 |
| WO | WO0045885 | 8/2000 |
| WO | WO0132398 | 5/2001 |
| WO | WO0143944 | 6/2001 |
| WO | WO0236194 | 5/2002 |

* cited by examiner

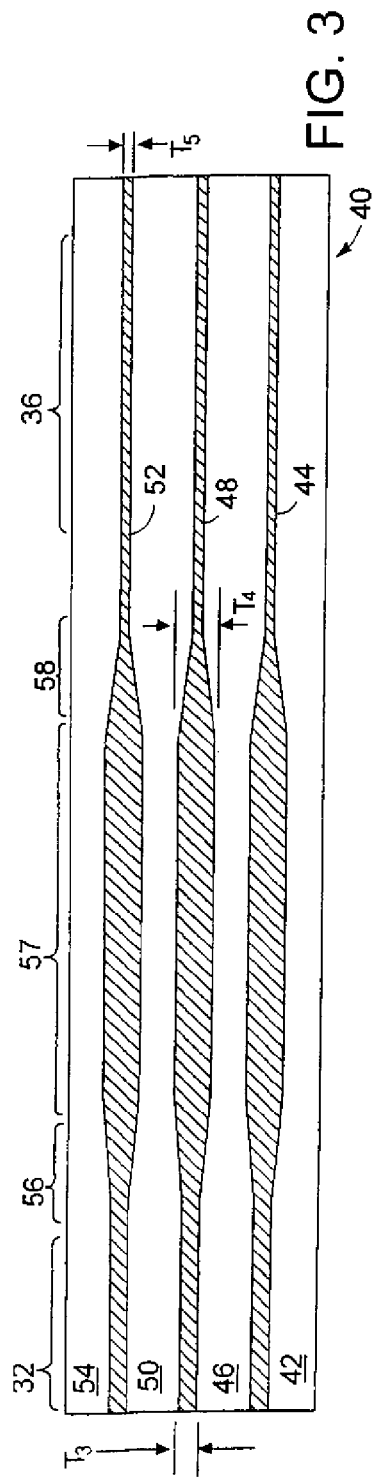
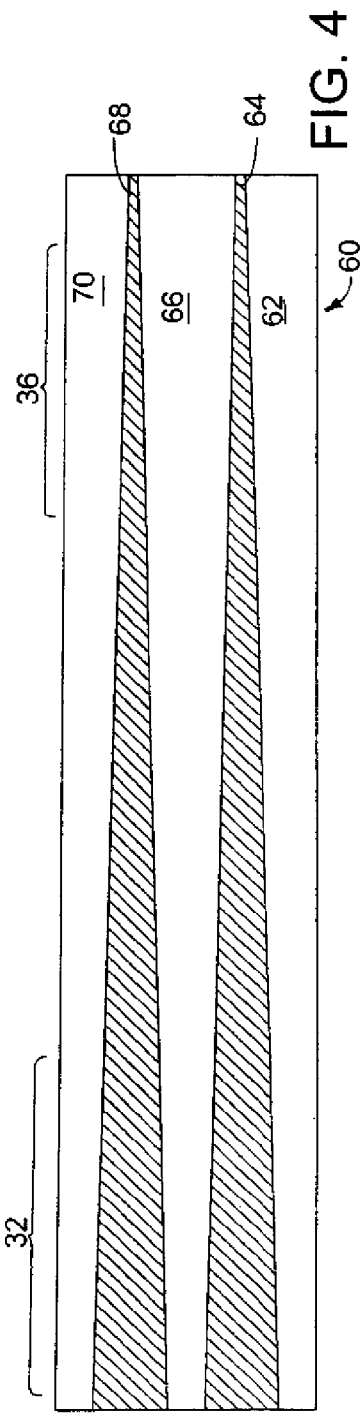
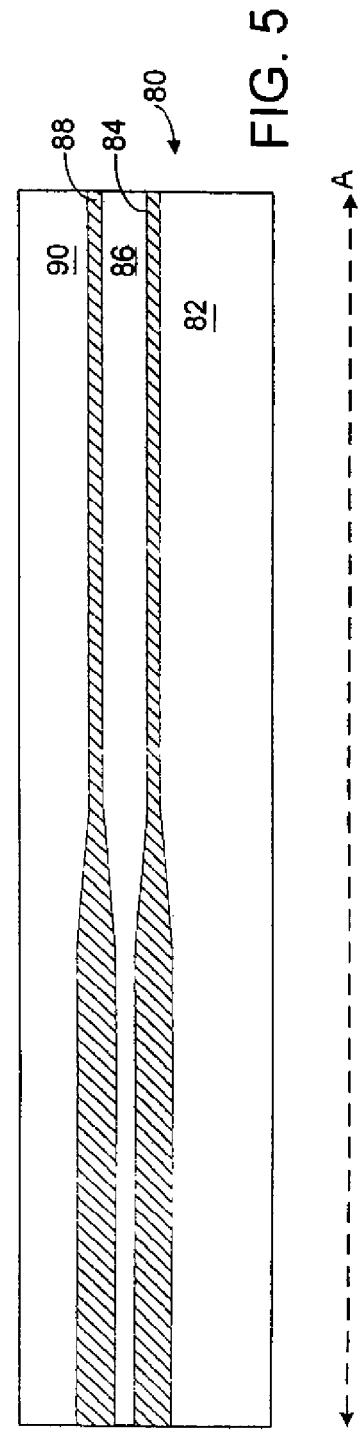

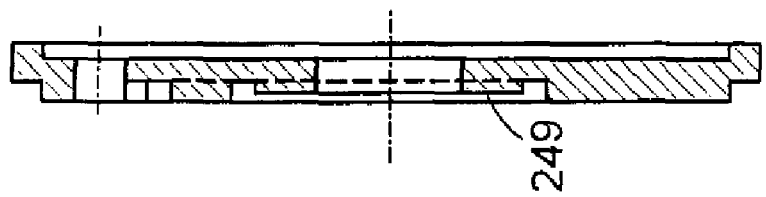
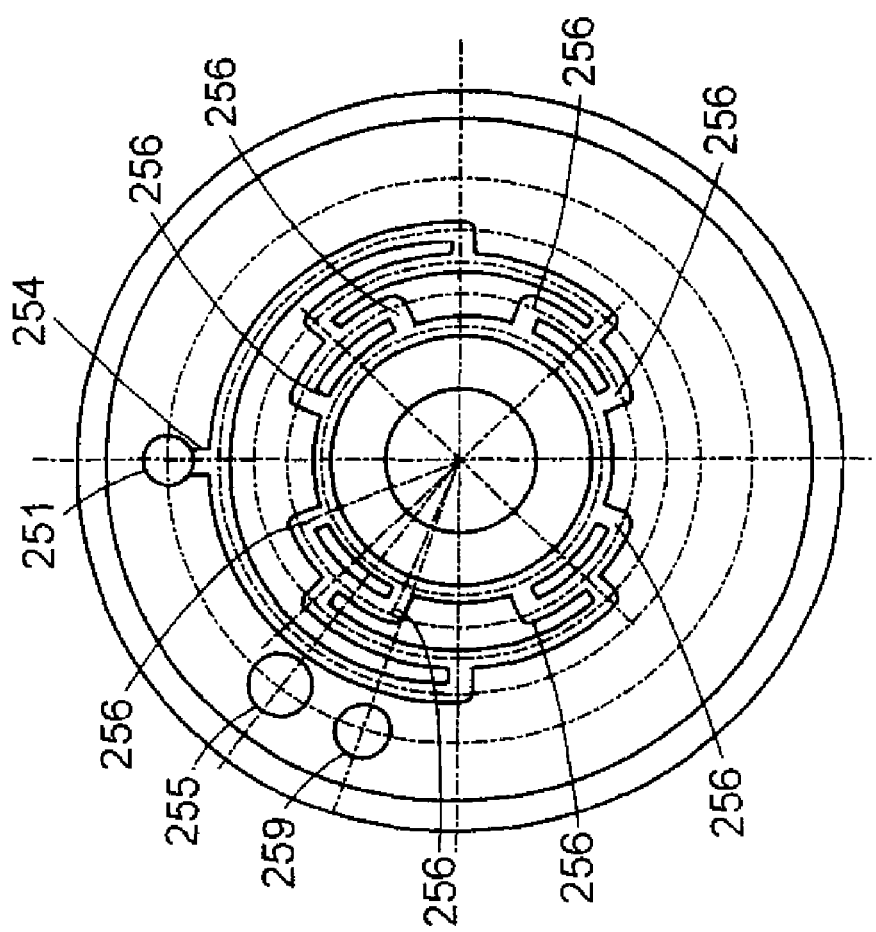
FIG. 11d-2
FIG. 11d-1

MULTILAYER MEDICAL DEVICES

RELATED APPLICATION

This application is a continuation of U.S. application Ser. No. 11/640,093, filed Dec. 15, 2006, which is a continuation of U.S. application Ser. No. 10/645,014, filed Aug. 21, 2003, now U.S. Pat. No. 7,166,099, the entire disclosures of which are both incorporated herein by reference.

This patent application is related to U.S. patent application Ser. No. 10/645,055, entitled "Medical Balloons," filed Aug. 21, 2003, the entire disclosure of which is incorporated herein by reference.

TECHNICAL FIELD

The invention relates to multilayer medical devices, such as, for example, medical tubing, guide wires, and catheters.

BACKGROUND

Intravascular medical devices such as, for example, guide wires, catheters, and medical tubing, allow physicians to perform a medical procedure, such as angioplasty or delivery of an endoprosthesis. In some cases, a device is inserted into a patient's vascular system at a convenient site and subsequently delivered, e.g., pushed, through the vascular system to a target site. The path that the device takes through the vascular system to the target site can be relatively tortuous, for example, requiring the device to change direction frequently.

In some circumstances, it is desirable for the device to have relatively good trackability so that it can travel along the tortuous path. At the same time, the device preferably has good pushability so that forces applied proximally to the device can be transmitted distally to deliver the device.

SUMMARY

The invention relates to multilayer medical devices, such as, for example, medical tubing, guide wires, and catheters.

In one aspect, the invention features a medical device having variable or differential stiffness along a length, e.g., the axial length, of the device. For example, a medical device may include a first portion, e.g., a proximal portion, that is relatively stiffer that a second portion, e.g., a portion distal of the first portion. As a result, in some embodiments, the device can have good trackability, e.g., at the relatively more flexible distal portion, and/or good pushability, e.g., at the relatively stiffer proximal portion.

In another aspect, the invention features a medical device including at least four layers including a first material and a second material having a different stiffness than a stiffness of the first material, wherein at least one of the layers varies in thickness axially along the device.

Embodiments may include one or more of the following features. The device is stiffer at a proximal end than at a distal end. The device includes at least five layers, e.g., at least seven layers or at least 13 layers. The device has the same number of layers for substantially the entire length of the device.

Various embodiments of layers are possible. The layers can extend substantially the length of the device. At least one of the layers can vary in thickness for substantially the entire length of the device. At least one of the layers can vary in thickness at a selected portion of the device. At least one of the layers can vary in thickness at more than the one selected portions of the device. The layers of different materials can vary in thickness at different selected portions of the device and/or at about the same selected portion of the device.

Various embodiments of materials are possible. The first and second materials can alternate. The first and second materials can include block copolymers including common block moieties, such as amide segments and tetramethylene glycol segments. The first and/or second material can be selected from a group consisting of thermoplastic polyamides, thermoplastic polyesters, and thermoplastic elastomers. The first and/or second material can be a blend of polymers.

The device can be an extruded device. The device can be in the form of a tube, a catheter shaft, or a guide wire.

In another aspect, the invention features a medical device including a first layer formed of a first material, a second layer formed of a second material having a different stiffness than a stiffness of the first material, and a third layer comprising an adhesive material between the first and second layers, wherein the first layer varies in thickness along an axial portion of the device.

In another aspect, the invention features a method of making a medical device. The method includes forming a tube including at least three layers formed of a first material and a second material having a different stiffness than a stiffness of the first material, and varying the thickness of at least one of the layers axially along the device. The method can include co-extruding the layers. The method can include forming the tube into a guide wire.

Embodiments may have one or more of the following advantages. The medical devices can have one or more relatively gradual transitions between portions having different stiffness, materials, and/or hardness. As a result, the devices can be less susceptible to kinking or buckling, which can occur in devices having abrupt changes, e.g., in stiffness, materials, and/or hardness. The physical properties, e.g., stiffness, of the devices, can be customized. The medical devices can be more resistant to damage.

Other aspects, features and advantages of the invention will be apparent from the description of the preferred embodiments and from the claims.

BRIEF DESCRIPTION OF DRAWINGS

FIG. 3 is a cross-sectional view of an embodiment of a wall of medical device.

FIG. 4 is a cross-sectional view of an embodiment of a wall of medical device.

FIG. 5 is a cross-sectional view of an embodiment of a wall of medical device.

FIG. 9a-1 is a cross-sectional view of the first crosshead disc in FIG. 9 according to one embodiment; and FIG. 9a-2 is a side cross-sectional view of the disc of FIG. 9a-1.

FIG. 9b-1 is a cross-sectional view of the second crosshead disc in FIG. 9 according to one embodiment; and FIG. 9b-2 is a side cross-sectional view of the disc of FIG. 9b-1.

FIG. 9c-1 is a cross-sectional view of the third, fifth, seventh, ninth, and eleventh crosshead discs in FIG. 3 according to one embodiment; and FIG. 9c-2 is a side cross-sectional view of the disc of FIG. 9c-1.

FIG. 9d-1 is a cross-sectional view of the fourth, sixth, eighth, tenth and twelfth crosshead discs in FIG. 3 according to one embodiment; and FIG. 9d-2 is a side cross-sectional view of the disc of FIG. 9d-1.

FIG. 9e-1 is a cross-sectional view of the thirteenth crosshead disc in FIG. 9 according to one embodiment; and FIG. 9e-2 is a side cross-sectional view of the disc of FIG. 9e-1.

FIG. 9f-1 is a cross-sectional view of assembly sections 226 and 228 according to one embodiment; and FIG. 9f-2 is a side cross-sectional view of the disc of FIG. 9f-1.

FIG. 9g-1 is a cross-sectional view of assembly section 224 according to one embodiment; and FIG. 9g-2 is a side cross-sectional view of the disc of FIG. 9g-1.

FIGS. 9h-1 and 9h-2 are cross-sectional views of assembly section 222 according to one embodiment; and FIG. 9h-3 is a side cross-sectional view of the assembly section of FIGS. 9h-1 and 9h-2.

FIG. 9i is a cross-sectional view of a mandrel according to one embodiment.

FIG. 9j-1 is a cross-sectional view of assembly section 230 according to one embodiment; and FIG. 9j-2 is a side cross-sectional view of the disc of FIG. 9j-1.

FIG. 9k-1 is a cross-sectional view of the nozzle according to one embodiment; and FIG. 9k-2 is a side cross-sectional view of the disc of FIG. 9k-1.

FIG. 11a-1 is a cross-sectional view of the first crosshead disc in FIG. 9 according to one embodiment; and FIG. 11a-2 is a side cross-sectional view of the disc of FIG. 11a-1.

FIG. 11b-1 is a cross-sectional view of the second crosshead disc in FIG. 9 according to one embodiment; and FIG. 11b-2 is a side cross-sectional view of the disc of FIG. 11b-1.

FIG. 11c-1 is a cross-sectional view of the third, fifth, seventh, ninth, and eleventh crosshead discs in FIG. 3 according to one embodiment; and FIG. 11c-2 is a side cross-sectional view of the disc of FIG. 11c-1.

FIG. 11d-1 is a cross-sectional view of the fourth, sixth, eighth, tenth and twelfth crosshead discs in FIG. 3 according to one embodiment; and FIG. 11d-2 is a side cross-sectional view of the disc of FIG. 11d-1.

FIG. 11e-1 is a cross-sectional view of the thirteenth crosshead disc in FIG. 9 according to one embodiment; and FIG. 11e-2 is a side cross-sectional view of the disc of FIG. 11e-1.

DETAILED DESCRIPTION

Figure 1:
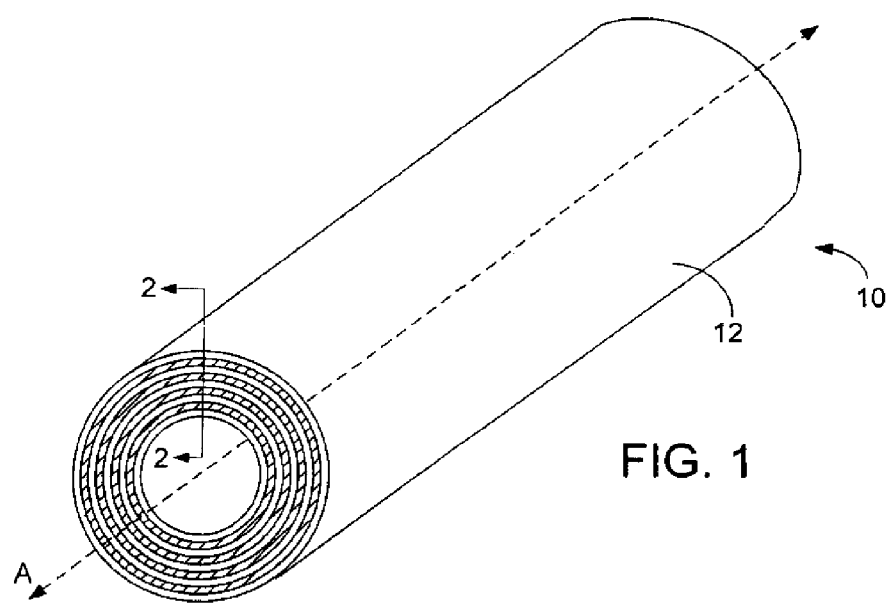
FIG. 1 is an illustration of a multilayer tube.
Figure 2:
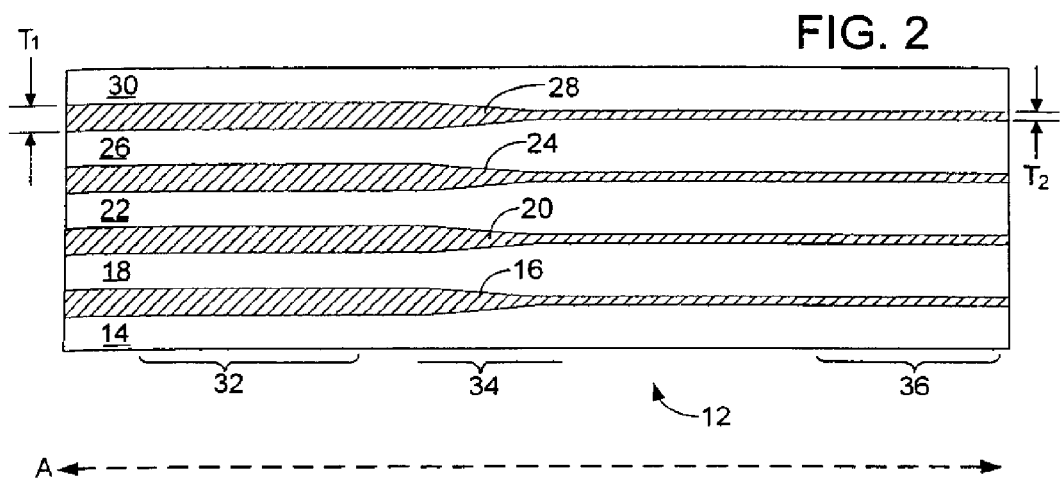
FIG. 2 is a cross-sectional view of a wall of the tube of FIG. 1, taken along line 2-2.

Referring to FIGS. 1 and 2, a tube 10 having variable or differential stiffness along its length (longitudinal or axial axis A) is shown. Tube 10 includes a wall 12 of constant thickness formed of multiple layers, in this example, nine, thin layers, 14, 16, 18, 20, 22, 24, 26, 28, and 30. Layers 14, 18, 22, 26, and 30 are formed of a first material, and alternate with layers 16, 20, 24, and 28, which are formed of a second material different than the first material, e.g., having different composition, strength, hardness, and/or stiffness. As shown, layers 14, 16, 18, 20, 22, 24, 26, 28, and 30 vary in thickness along axis A of tube 10. Layers 16, 20, 24, and 28 have a thickness $T_1$ at a proximal portion 32 of tube 10, decrease distally in thickness at a selected transition portion 34 of the tube, and have a thickness $T_2$, which is less than $T_1$, at a distal portion 36. Conversely, layers 14, 18, 22, 26, and 30 are generally thicker at distal portion 36 than at proximal portion 34, and vary in thickness at portion 34. By controlling the thickness of one or more layers of tube 10, the stiffness of the tube along axis A can be controlled.

For example, layers 14, 18, 22, 26, and 30 can be formed of the first material, such as PEBAX® 7033 (69 Shore D, available from Atofina, Philadelphia, Pa.) and layers 16, 20, 24, and 28 can be formed of a stiff (relative to the first material) second material, such as PEBAX® 7233 (72 Shore D). By distally decreasing the thickness of layers 16, 20, 24, and 28, the amount of stiff material at distal portion 36 also decreases relative to the amount of stiff material at proximal portion 34. As a result, since there is less stiff material at distal portion 36, i.e., more flexible material, the distal portion is more flexible than proximal portion 32. Thus, when tube 10 is formed, for example, into a guide wire or a catheter (e.g., a balloon catheter), relatively stiff proximal portion 32 can provide the tube with good pushability, while relatively flexible distal portion 36 can provide the tube with good trackability to navigate through tortuous paths.

Without wishing to be bound by theory, it is believed that the multitude of layers provides tube 10 with a relatively gradual transition between different portions or layers of materials, and differing physical properties, e.g., stiffness. It is believed that an abrupt transition can cause a tube to be more susceptible to unpredictable kinking or buckling, which can occur during use and is typically undesirable. By using a multitude of layers, the materials are distributed evenly to approximate homogenous blending or mixing of the materials, e.g., as in a solid solution, so that there is a reduced possibility of a localized concentration of a material that can disproportionately contribute to tube 10.

The stiffness of a portion of tube 10 can be controlled by controlling design parameters such as, among others, the materials used in the layers and their amounts (e.g., concentrations), the placement of the materials in a radial direction of the tube, and/or the number of layers the tube includes, which is related to the placement of the materials. Generally, stiffer materials tend to provide stiffer tubes or tube portions. For substantially similar tubes, a tube having a higher amount or concentration of a stiff material tends to be stiffer than another tube having a lower amount or concentration of the stiff material. For example, a first portion of a tube having a ratio of PEBAX® 7233 (72 Shore D) to PEBAX®7033 (69 Shore D) of 3:1 is typically stiffer than a second tube portion having a PEBAX® 7233:PEBAX® 7033 ratio of 2:1 because the first portion has more stiff material (PEBAX® 7233) than the second portion.

The placement of the materials in a radial direction of the tube also affects the stiffness of the tube or tube portion. In some embodiments, forming one or more layers of a stiff material radially farther or away from axis A typically increases the stiffness of the tube. For example, a two-layer tube having flexible material as an inner layer (closer to axis A) and stiff material as an outer layer tends to be stiffer than a two-layer tube in which the flexible material is formed as the outer layer and the stiff material is formed as the inner layer. It is believed that the farther away a layer is from axis A, the more effect the layer can have on the moment of inertia of a tube. For example, a stiff layer radially farther away from axis A can enhance the stiffness of a tube more than when the stiff layer is radially closer to axis A.

Related to the placement of materials is the number of layers that a tube includes. For example, assuming the tube wall thickness remains constant, a two-layer tube portion having flexible material as the inner layer and stiff material as the outer layer tends to be more stiff than a four-layer tube portion having alternating layers of flexible material and stiff material, in which the innermost layer is formed with flexible material. In the two-layer portion, all the soft material is in one layer and is close to axis A. In comparison, in the four-layer portion, some of the stiff material has been formed radially closer to axis A. As described above, forming a stiff material radially farther from axis A enhances the stiffness of the tube. Thus, in this example, increasing the number of layers and forming the stiffer material closer to axis A (or forming more flexible material farther away from axis A) decreases the stiffness of the tube. This example assumes that the ratio of stiff to flexible materials remain the same, but generally, the stiffness of a portion of the tube is dependent on multiple (e.g., all) of the design parameters. The effects of the concentrations of materials, the number of layers, and their radial placement on the stiffness of a tube are presented in Example 1 below.

The number of layers is generally two or more. For example, the number of layers can be at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, or more. In certain embodiments, the number of layers is less than 100 (e.g., less than 90, less than 80, less than 70, less than 60, less than 50, less than 40, less than 35, less than 30, less than 25, less than 20, less than 15, or less than 10). The number of layers may be, for example, seven, thirteen, twenty or more.

One or more of the layers varies in thickness along the length of tube 10. As shown in FIG. 2, the layers, e.g., layers 16, 20, 24, and 28, can have a first constant thickness, e.g., at proximal portion 32 and a second constant thickness different than the first thickness, e.g., less than the first thickness at distal portion 36. Between portions 32 and 36, as shown, at transition portion 34, the thickness of the layers changes in thickness. Similarly, layers 14, 18, 22, 26, and 30 are generally thicker at distal portion 36 than at proximal portion 34, and vary in thickness at transition portion 34. One or more of the layers can have more than two different portions having different thickness.

Figure 8:
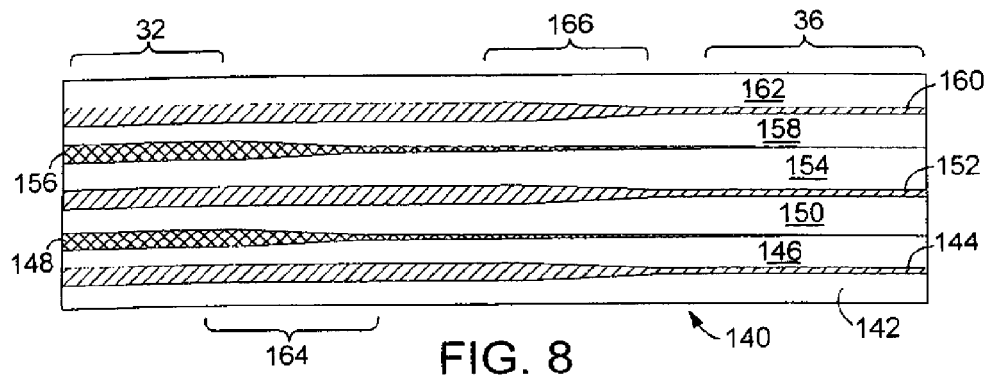
FIG. 8 is a cross-sectional view of an embodiment of a wall of medical device.

In other embodiments, a tube includes more than one transition portions 34, e.g., two, three, four, five, more than five, more than ten, etc. Referring to FIG. 3, a tube wall 40 includes seven layers, 42, 44, 46, 48, 50, 52, and 54 formed of two different materials. Layers 44, 48, and 52 vary in thickness from a first thickness $T_3$ at proximal portion 32, through a first transition portion 56, to an intermediate portion 57 having a second thickness $T_4$, through a second transition portion 58, and to a third thickness $T_5$ at distal portion 36. As shown, $T_4 > T_3 > T_5$. In some embodiments, if layers 44, 48, and 52 are formed of a material stiffer than the material of layers 42, 46, 55, and 54, then intermediate portion 57 is the stiffest portion, followed by the portion proximal of the intermediate portion, and followed by the portion distal of the intermediate portion. In some embodiments, one or more of layers 42-54 can be made of different materials. Transition portions 56 and 58 can be located at different axial positions, as described below (FIG. 8). Within a layer, the composition can change, for example, layer 44 can change from a soft material to a stiff material to soft material.

In certain embodiments, the layers vary in thickness along the entire length of a tube. Referring to FIG. 4, a tube wall 60 includes five layers 62, 64, 66, 68, and 70 formed of two different materials. Layers 64 and 68 decrease in thickness from proximal portion 32 to distal portion 36. If layers 64 and 68 are formed of a material stiffer than the material of layers 62, 66, and 70, then distal portion 36 tends to be less stiff than proximal portion 32. If layers 64 and 68 are formed of a material more flexible than the material of layers 62, 66, and 70, then distal portion 36 tends to be stiffer than proximal portion 32. In other embodiments, the layers vary in thickness along less than the entire length of tube 10, e.g., less than 90%, 80%, 70%, 60%, 50%, 40%, 30%, or 20%, as determined from either end of the tube.

The layers can be asymmetrically distributed in the radial direction of the tube. For example, referring to FIG. 5, a tube wall 80 includes five layers 82, 84, 86, 88, and 90 formed of two materials. Layers 84 and 88 are arranged closer to an outer surface of tube wall 80 than to an inner surface. In other embodiments, the layers can be evenly distributed along in the radial direction of the tube (e.g., as shown in FIG. 2).

Figure 6:
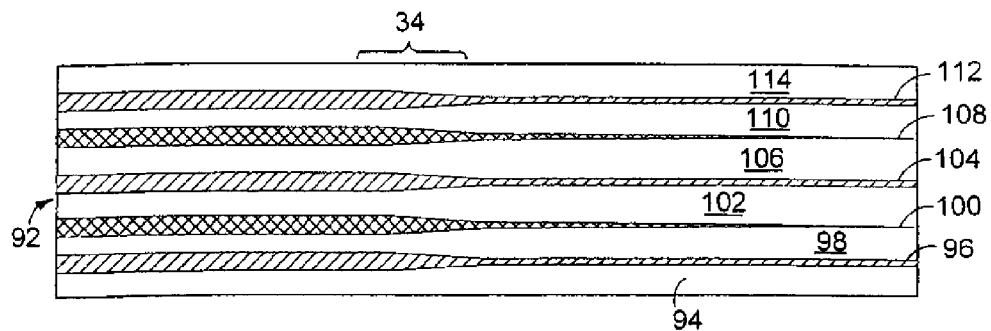
FIG. 6 is a cross-sectional view of an embodiment of a wall of medical device.

Tube 10 can be formed of two or more different materials, e.g., three, four, five, ten, or more. FIG. 6 shows a tube wall 92 having eleven layers 94, 96, 98, 100, 102, 104, 106, 108, 110, 112, and 114 formed of three materials. Layers 94, 98, 102, 106, 110, and 114 are formed of a first material; layers 96, 104, and 112 are formed of a second material; and layers 100 and 108 are formed of a third material. As shown, all the layers vary in thickness similarly to the embodiment shown in FIG. 2, e.g., having transition portions 34 generally at the same axial position. In other embodiments, a tube may include multiple transition portions located at different axial positions. Referring to FIG. 8, a tube 140 includes eleven layers 142, 144, 146, 148, 150, 152, 154, 156, 158, 160, and 162 formed of three materials. Layers 148 and 156 have a transition portion 164 that is more proximal than transition portion 166 of layers 144, 152, and 160. In some embodiments, layers 148 and 156 can be made of the same material as layers 144, 152, and 160. This configuration may enhance the transition to provide a relatively smooth transition.

Figure 7:
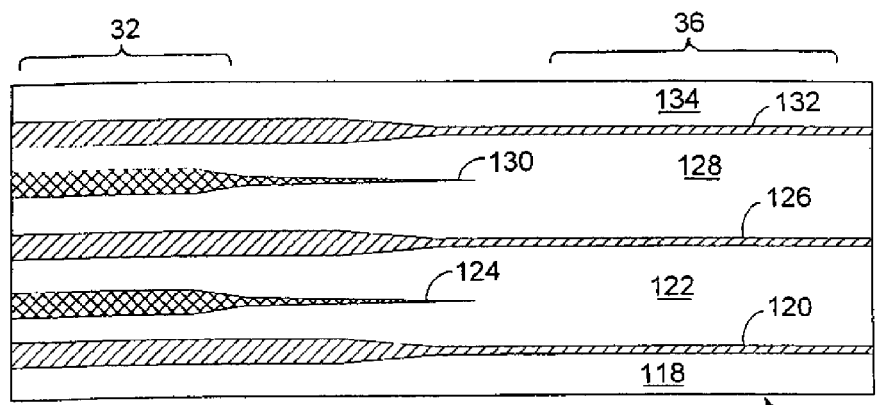
FIG. 7 is a cross-sectional view of an embodiment of a wall of medical device.

Alternatively or in addition, one or more of the layers can terminate within the tube wall. Referring to FIG. 7, a tube wall 116 formed of three different materials includes two layers 124 and 130 that terminate along the length of the tube wall. As a result, at proximal portion 32, tube wall 16 includes eleven layers formed of layers 118, 120, 122, 124, 126, 128, 130, 132, and 134; and at distal portion 36, the tube wall includes seven layers formed of layers 118, 120, 122, 126, 128, 132, and 134.

A tube can have any combination of the layers described above, formed of two or more materials. For example, a tube can have one or more layers of layer 16, layer 44, and/or layer 64, arranged evenly apart or asymmetrically (e.g., as shown in FIG. 5). One or more layers of layer 16, layer 44, and/or layer 64 can have one or more transition portions (e.g., as shown in FIGS. 6 and 8). The number of layers can change along the axial direction of the tube.

In certain embodiments, one or more layers can have along their axial lengths a minimum thickness of at least about 0.02 micron (e.g., at least about 0.05 micron, at least about 0.1 micron, at least about 0.25 micron, at least about 0.5 micron, at least about 0.75 micron, at least about one micron, at least about 1.5 microns, at least about 2 microns, at least about 2.5 microns, at least about 3 microns, at least about 3.5 microns), and/or a maximum thickness of at most about 20 microns (e.g., at most about 15 microns, at most about 10 microns, at most about nine microns, at most about eight microns, at most about seven microns, at most about six microns, at most about five microns, at most about four microns, at most about three microns, at most about two microns, at most about one micron, at most about 0.5 micron, at most about 0.25 micron). The thicknesses of the layers are dependent on, e.g., the thickness of the device being formed, the number of layers, the materials of the layers, and/or the configurations of the layers.

Along a portion of a tube, the thickness of the flexible and stiff layers may be different or the same. In some relatively stiff portions, the flexible layers make up from about one percent to about 45% (e.g., from about 5% to about 45%, from about 5% to about 40%, about 30% or less, from about 20% to about 30%) of the total tube wall thickness and stiff polymer makes up the balance. In certain relatively flexible portions, the stiff layers make up from about one percent to about 45% (e.g., from about 5% to about 45%, from about 5% to about 40%, about 30% or less, from about 20% to about 30%) of the total tube wall thickness and flexible polymer makes up the balance. As a result, for a device with a comparable number of flexible and stiff layers, the flexible polymer layers may be thinner or thicker than the stiff polymer layers. The thickness of the layers may vary progressively in a radial direction. For example, the layers may get thicker from the outermost layer to the innermost layer or vice versa. The thickness of the layers of one type (flexible or stiff) may vary while the layers of the other type are constant.

In some embodiments, layers may be formed of stiff or hard polymer that has a hardness of more than about 60 Shore D, preferably 65 Shore D or more, and softer polymer that has a hardness of about 60 Shore D or less. In some embodiments, the flexible or soft polymer can have a hardness of greater than about 60 Shore D, but it is still softer than the hard polymer. The difference in hardnesses of adjacent bonded layers can be about 40 Shore D or less, preferably 20 Shore D or less, which can enhance compatibility between the layers, reduce delamination at the interface, and/or increase ease of coextruding. Hardness may be measured according to ASTM D2240. The layers can alternate between hard and soft polymer. The layers may be of progressively increasing hardness. For example, the layers may be of progressively increasing hardness from the outermost layer to the innermost layer. For example, for a support used for stent delivery, the outermost layer can be a soft layer that absorbs and distributes stress and abrasion imposed by the stent.

The layers may be of substantially pure polymer or they may be blends of different polymers. All of the soft (or hard) layers may be made of the same soft (or hard) polymer or the different soft (or hard) layers may be made of different polymers. The soft and hard can be made of block copolymers including common block moieties, which can enhance compatibility, while maintaining defect retardation. For example, the block moieties may be amide segments and tetramethylene glycol segments.

An example is the PEBAX® family of polymers, which can be used pure or as blends (available from Atofina, Philadelphia, Pa.). For example, PEBAX® 5533 (55 Shore D) can be blended with PEBAX® 2533 (25 Shore D) in a weight ratio of about 4 to 1 to provide a soft polymer of about 50 Shore D. Another combination of hard and soft polymers is polybutylene terephthalate (PBT) such as CELANEX® (over 80 Shore D, from Ticona, Summit, N.J.) and polyester/ether block copolymer available as ARNITEL® (55 Shore D, from DSM, Erionspilla, Ind.). A combination of hard and soft polymers is PBT and one or more PBT thermoplastic elastomers, such as RITEFLEX® (55 Shore D from Ticona in Summit, N.J.) and HYTREL® (55 Shore D from E. I. Dupont de Nemours, Wilmington, Del.) for example. Still another combination of hard and soft polymers is polyethylene terephthalate (PET) and a thermoplastic elastomer, such as a PBT thermoplastic elastomer (e.g., ARNITEL®, HYTREL®, or RITEFLEX®).

In certain embodiments, one or more layers can contain one or more nylons. For example, one or more of the hard polymer layers can contain one or more nylons. For example, a combination of hard and soft polymers is a nylon and a PEBAX®-type material, such as PEBAX®, GRILON®, GRILAMID® (EMS) and/or VESTAMID® (Creanova). Examples of nylons include aliphatic nylons, such as Nylon 11 (Elf Atochem), Nylon 6 (Allied Signal), Nylon 6/10 (BASF), Nylon 6/12 (Ashley Polymers) and Nylon 12. Additional examples of nylons include aromatic nylons, such as GRIVORY® (EMS) and Nylon MXD-6. Other nylons and/or combinations of nylons can be used.

In some embodiments, one or more layers can contain a liquid crystal polymer (LCP) (e.g., a composite material having the LCP incorporated therein). Examples of LCPs include polyester(s), polyamide(s) and/or their copolymers, such as VECTRA® A (Ticona), VECTRA® B (Ticona) and VECTRA® LKX (Ticona) (e.g., VECTRA® LKX 1111 (Ticona)). Other LCPs and/or combinations of LCPs can be used.

The LCP can be incorporated into one or more polymers, such as, for example, a PEBAX®-type material, a nylon, a thermoplastic polyester and/or thermoplastic elastomer versions thereof. In certain embodiments, the liquid crystal polymer can be incorporated into one or more of the polymer layers to form a hard layer of material (e.g., a layer of material with more than about 60 Shore D hardness, such as more than about 65 Shore D hardness). In a preferred combination, an LCP is incorporated into a layer containing one or more PEBAX®-type materials, such as PEBAX®, GRILON®, GRILAMID®, and/or VESTAMID®. In certain embodiments, an LCP-containing composition can be relatively stiff in the direction of melt flow. Without wishing to be bound by theory, it is believed that this may result because LCP crystals (e.g., fibers) form or align in the melt flow direction as the polymer composite cools from a liquid state to a solid state.

The amount of LCP contained in the tube can vary depending upon its intended use. In some embodiments, as the percentage of LCP in a composite material is decreased, the individual layer thickness and the overall thickness of one or more layers of an LCP-containing composite material, e.g., in a tube, can be increased.

The LCP content of a tube can be at least about 0.1 weight percent, such as from about 0.1 weight percent to about 20 weight percent (e.g., from about 0.5 weight percent to about 10 weight percent, from about one to about five weight percent). Within a given layer, the LCP content can be at least about 0.1 weight percent (e.g., from about one weight percent to about 50 weight percent, from about five weight percent to about 20 weight percent, from about five weight percent to about 15 weight percent).

The percentage of layers containing LCP relative to the total number of layers can be from about one percent to about 80 percent (e.g., at least about five percent, at least about 10 percent, at least about 15 percent, at least about 20 percent, at least about 25 percent, at least about 30 percent, at least about 35 percent, at least about 40 percent, at most about 80 percent, at most about 75 percent, at most about 70 percent, at most about 65 percent, at most about 60 percent, at most about 55 percent, at most about 50 percent, at most about 45 percent).

In certain embodiments, an adhesion enhancing material can be incorporated into one or more material layers. An adhesion enhancing material can be used, for example, to enhance the adhesion between adjacent layers. Examples of adhesion enhancing materials include epoxy or anhydride modified polyolefins, such as LOTADER® (Elf Atochem) and KODAR® PETG (Eastman Kodak). An adhesion enhancing material can be added to a material (e.g., a composition containing one or more polymers) prior to extrusion (described below). For example, in embodiments in which alternate layers are formed of PET and PBT, PETG can be added to the PET before extrusion.

The amount of adhesion enhancing material can vary depending upon the intended use. In some embodiments, a sufficient amount of adhesion enhancing material(s) are included in the material so that the adhesion enhancing material(s) makes up at least about 0.5 percent of the resulting mixture that forms the layer (e.g., at least about one percent, at least about five percent, at least about 10 percent) and/or at most about 20 percent of the resulting mixture that forms the layer (e.g., at most about 15 percent, at most about 12 percent, at most about 10 percent).

In certain embodiments, the adhesion between one or more adjacent layers can vary as layer thickness is varied. Generally, embodiments can provide adhesion between one or more (e.g., all) layers in a medical device (e.g., a tube). For example, one or more (e.g., all) layers in a medical device (e.g., a tube) can demonstrate good adhesion when flexed, deflated and/or inflated. In some embodiments, a medical device (e.g., a tube) can show good flexibility and/or adhesion (e.g., when one or more layers are relatively thin).

In some embodiments, a compatibilizing material can be incorporated into one or more material layers. The compatibilizing material can be designed, for example, to modify one or more phase boundaries of the LCP(s) and one or more of the other polymer(s) (e.g., thermoplastic polymer(s)) and/or to enhance adhesion between the LCPs and one or more of the other polymer(s). The compatibilizing material can be a copolymer, such as a block copolymer, including moieties of at least two different chemical structures, respectively providing compatibility with an LCP and one or more other polymers in the mixture. The compatibilizing material can be a reactive polymer that reacts with the LCP and/or one or more other polymers in the mixture. The compatibilizing material can be a catalyst that promotes a reaction between the LCP and one or more other polymers in the mixture. Other compatibilizing materials can be used. Combinations of compatibilizing materials can be used.

Examples of compatibilizing materials include copolyester elastomers, ethylene unsaturated ester copolymers, such as ethylene-maleic anhydride copolymers, copolymers of ethylene and a carboxylic acid or acid derivative, such as ethylene-methyl acrylate copolymers, polyolefins or ethylene-unsaturated ester copolymers grafted with functional monomers, such as ethylene-methyl acrylate copolymers, copolymers of ethylene and a carboxylic acid or acid derivative, such as ethylene-methyl acrylate maleic anhydride terpolymers, terpolymers of ethylene, unsaturated ester and a carboxylic acid or acid derivative, such as ethylene-methyl acrylate-methacrylic acid terpolymers, maleic acid grafted styrene-ethylene-butadiene-styrene block copolymers, and acrylic acid elastomers, such as acrylic rubbers. Similar polymers containing epoxy functional groups, for instance derived from glycidyl methylacrylate (e.g., alkyl(meth)acrylate-ethylene-glycidyl (meth)acrylate polymers) can be used. Ionomeric copolymers can be used. PETG can be used. Examples of compatibilizing materials include HYTREL® HTR-6108, POLYBOND® 3009 (BP Chemicals), SP 2205 (Chevron), DS 1328/60 (Chevron), LOTADER® 2400, ESCOR® ATX-320, ESCOR® ATX-325, VAMAC® G1 and LOTADER® AX8660. In certain embodiments, a compatibilizing material (e.g., PETG) can be mixed with one or more polymers (e.g., an LCP-containing material) prior to extrusion.

There are many ways in which LCPs can be blended into thermoplastics. The LCP blend can be a ternary system of LCP, thermoplastic and compatibilizing materials. Systems with multiple combinations of different LCPs, different thermoplastics and different compatibilizing materials are contemplated.

The compatibilized blend can be a blend of polyazomethine LCP, a thermoplastic polymer such as a polyamide, and a compatibilizing material such as a caprolactum having at least one functional group capable of showing compatibility and/or reactivity to the LCP and/or the thermoplastic polymer. Such blends are described, for example, in U.S. Pat. No. 5,565,530, which is hereby incorporated by reference.

One polymer blend product which can be used includes PET, a wholly aromatic LCP copolyester and an ethylene-methyl acrylate-acrylic acid terpolymer compatibilizing material, such as, for example, ESCOR® ATX320, ESCOR® ATX325, or ESCOR® XV-11.04. Another polymer blend product includes PET, a wholly aromatic LCP copolyester and an ethylene-maleic anhydride copolymer compatibilizing material, such as POLYBOND® 3009. Another polymer blend product includes PET, a wholly aromatic LCP copolyester and an ethylene-methyl acrylate copolymer grated with maleic anhydride compatibilizing material, such as DS 1328/60, or a copolyester elastomer, such as HYTREL® HTR 6108.

Polymer blend products including PET, LCP and at least two compatibilizing materials can be used. For example, DS 1328/60 and POLYBOND® 3009 can be used with the LCP VECTRA®. As an additional example, when the LCP is VECTRA®, the compatibilizing materials can be POLYBOND® 3009 and at least one additional compatibilizing material selected from ESCOR® ATX-320, ESCOR® ATX-325, DS 1328160, ESCOR® XV-11.04 and HYTREL® HTR-6108.

In certain embodiments, consideration is given to the properties of the LCP and the other polymer(s) (e.g., PET), as well as the desired properties of the resulting blend, when selecting the compatibilizing material(s).

In some embodiments containing an LCP, a thermoplastic polymer and compatibilizing material(s), the blend product includes from about 0.1 weight percent to about 10 weight percent (e.g., from about 0.5 weight percent to about 2 percent) LCP, from about 40 weight percent to about 99 weight percent (e.g., from about 85 weight percent to about 99 weight percent) thermoplastic polymer, and from about 0.1 weight percent to about 30 weight percent (e.g., from about one weight percent to about 10 weight percent) compatibilizing material(s).

While certain polymers and polymer combinations are discussed above, other polymers and polymer combinations can also be used. Other polymers include, for example, elastomers such as thermoplastic elastomers and engineering thermoplastic elastomers, such as polybutylene terephthalate-polyethene glycol block copolymers, which are available, for example, as HYTREL®. These are discussed in Hamilton U.S. Pat. No. 5,797,877, the entire content of which is incorporated herein by reference. Other polymers include polyurethenes. Other polymers include copolymers such as ABS (acrylonitrle-butadiene-styrene), ABS/nylon, ABS/polyvinyl chloride (PVC), ABS/polycarbonate, acrylonitrile copolymer, polyacrylamide, polyacrylate and polyacrylsulfone, polyesters such as polyethylene terephthalate (PET), polybutylene terephthalate (PBT), polyethylene naphthalate (PEN), liquid crystal polymer (LCP), polyester/polycaprolactone and polyester/polyadipate; and high melt temperature polyethers including polyetheretherketone (PEEK), polyethersulfone (PES), polyetherimide (PEI) and polyetherketone (PEK), polymenthylpentene, polyphenylene ether, polyphenylene sulfide, and styrene acrylonitrile (SAN), polyamides such as nylon 6, nylon 6/6, nylon 6/66, nylon 6/9, nylon 6/10, nylon 6/12, nylon 11, nylon 12, ethylene, propylene ethylene vinylacetate and ethylene vinyl alcohol (EVA), various ionomers, polyethylene type I-IV, polyolefins, polyurethane, polyvinyl chloride, and polysiloxanes (silicones). Those with low to medium melt temperatures include fluorocarbons such as polychlorotriethylene (CTFE), poly[ethylene-co-chlorotrifluoroethylene] (ECTFE) copolymer ethylene tetrafluoroethylene (ETFE), copolymer tetrafluoroethylene and hexafluoropropylene (FEP), perfluoroalkane (PFA) and poly[vinylidene fluoride] (PVDF).

The tubes can be prepared by an extrusion process. Generally, this process can involve the use of an extrusion apparatus (e.g., a crosshead, such as a compact crosshead) having a series of discs. For example, the apparatus can have one disc per material layer. Each disc can have one or more channels (e.g., one channel, two channels, three channels, four channels, five channels, six channels, seven channels, eight channels, 10 channels, 12 channels, 14 channels, 16 channels, etc.). In some embodiments, it can be desirable to have a relatively large number of channels (e.g., five, six, seven, eight, etc. channels) in at least one disc (e.g., in one disc, two discs, three discs, four discs, five discs, six discs, seven discs, eight discs, etc.) to enhance the degree of circularity of the layers. In some embodiments, each disc has a relatively large number of channels. The number of channels can be selected based upon, for example, the volumetric output, the temperature, the viscosity, the pressure drop, the outer diameter of the discs, the material (e.g., polymer(s)) used, and/or the channel dimensions.

Figure 9:
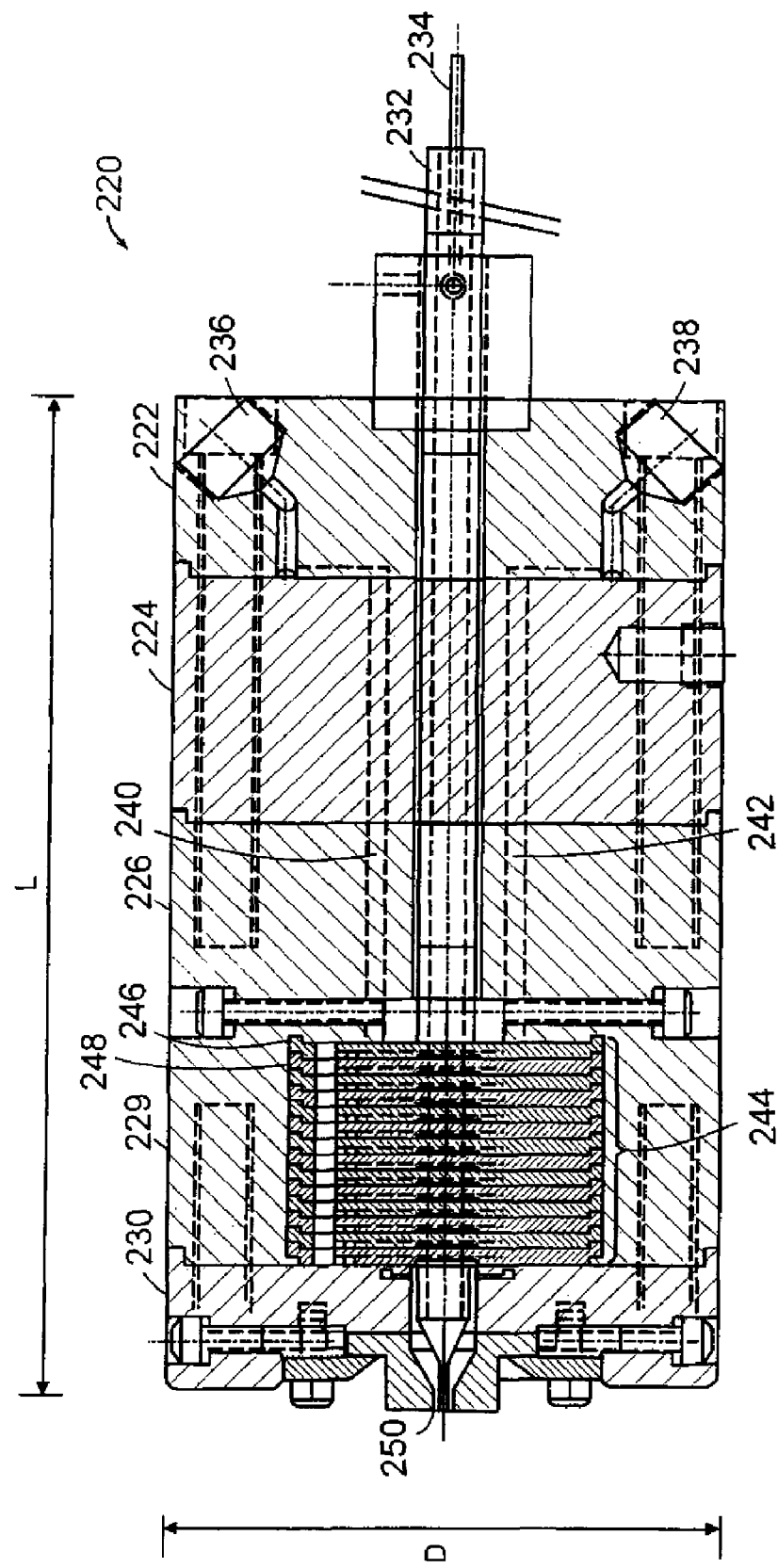
FIG. 9 is an assembly drawing of an extrusion crosshead.
Figures 2, 9A:
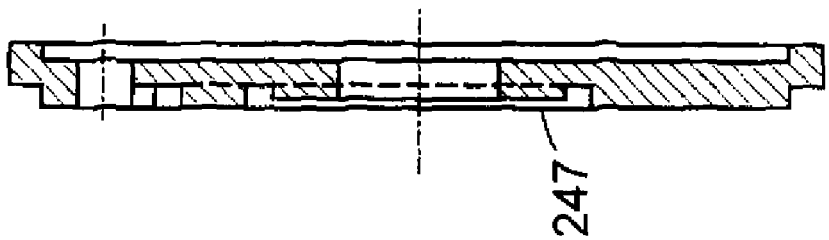
Figures 1, 9A:
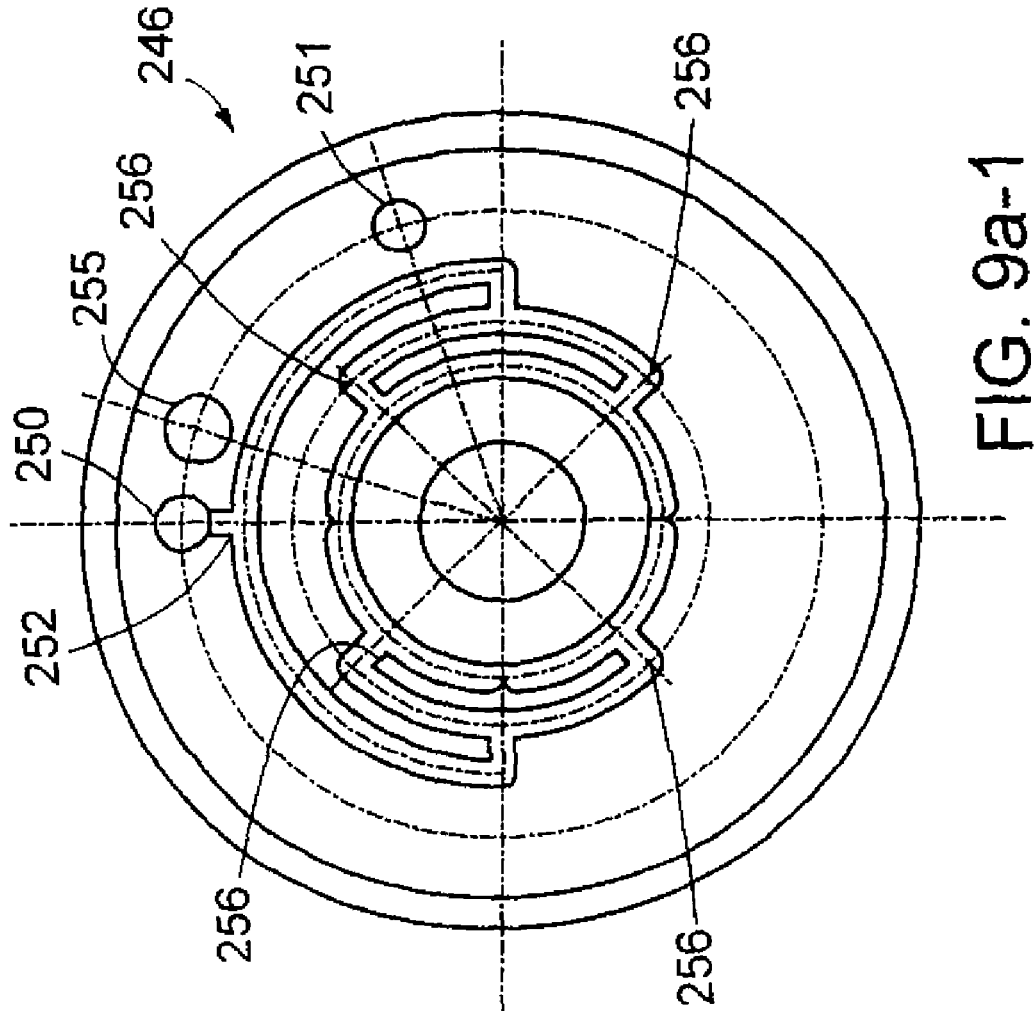
Figures 2, 9B:
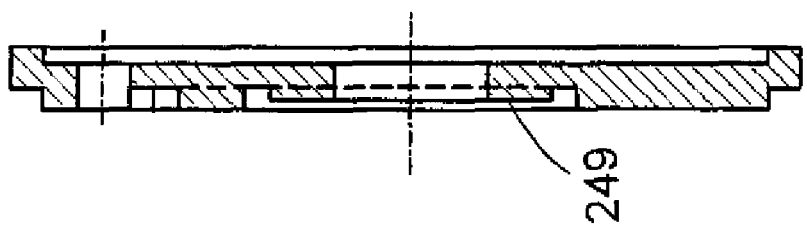
Figures 1, 9B:
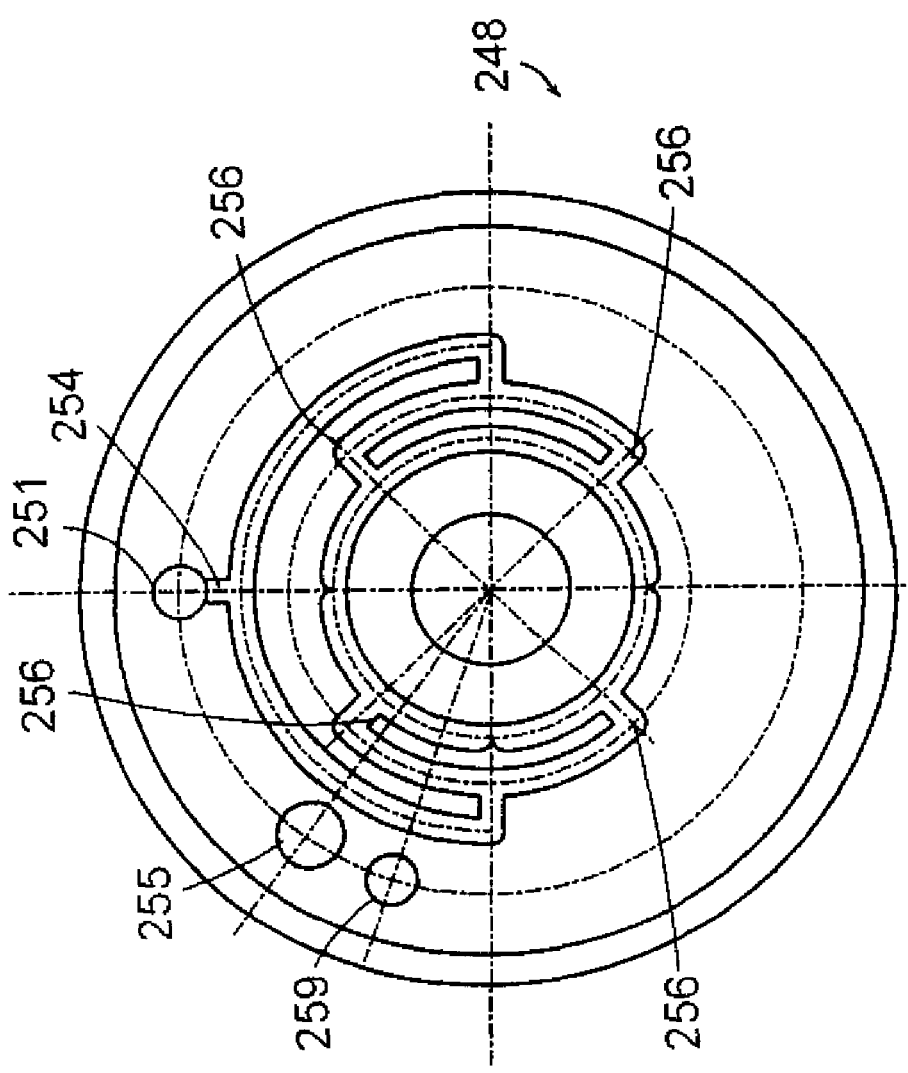
Figures 2, 9C:
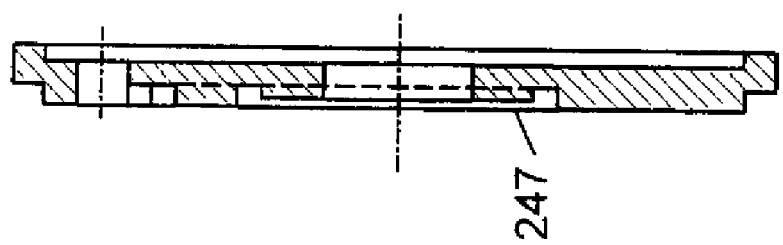
Figures 1, 9C:
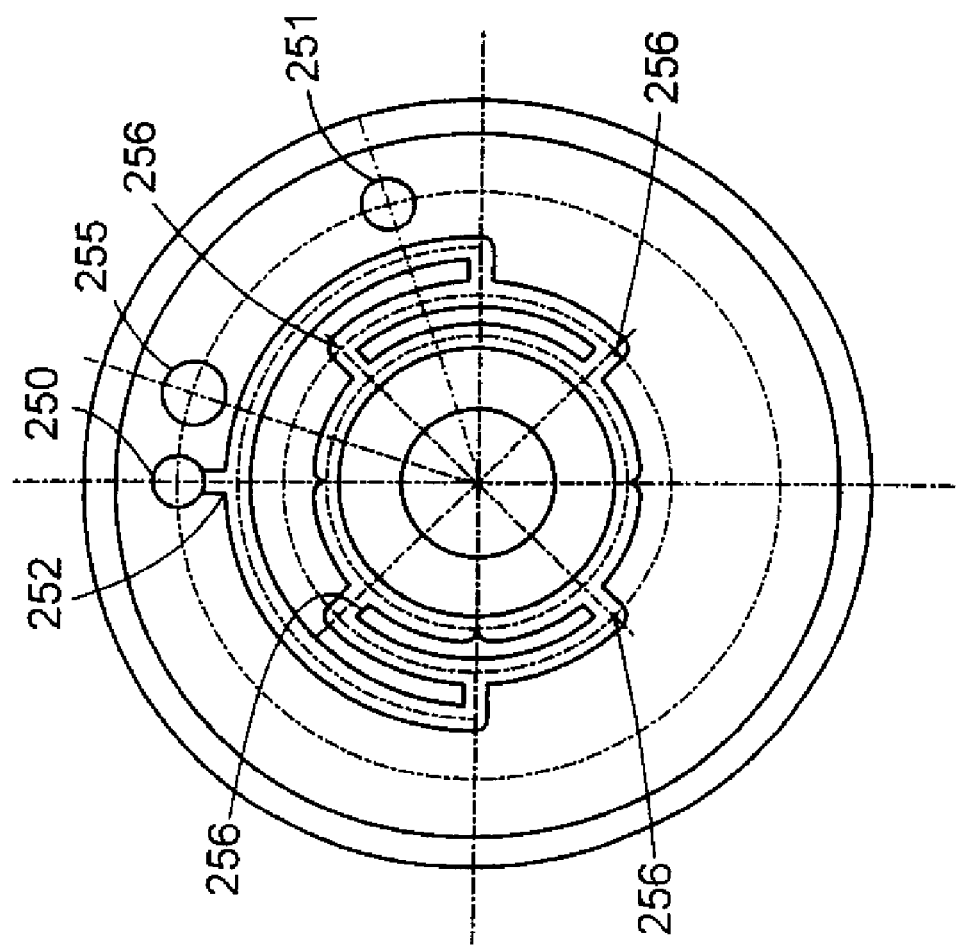
Figures 2, 9D:
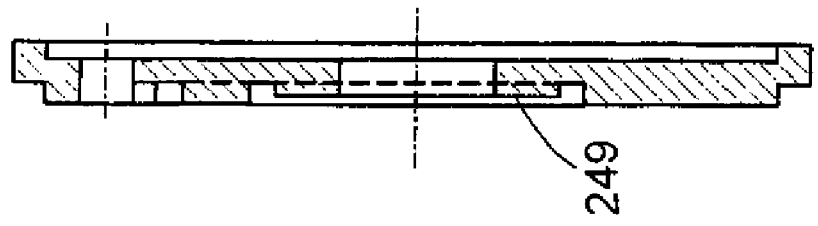
Figures 1, 9D:
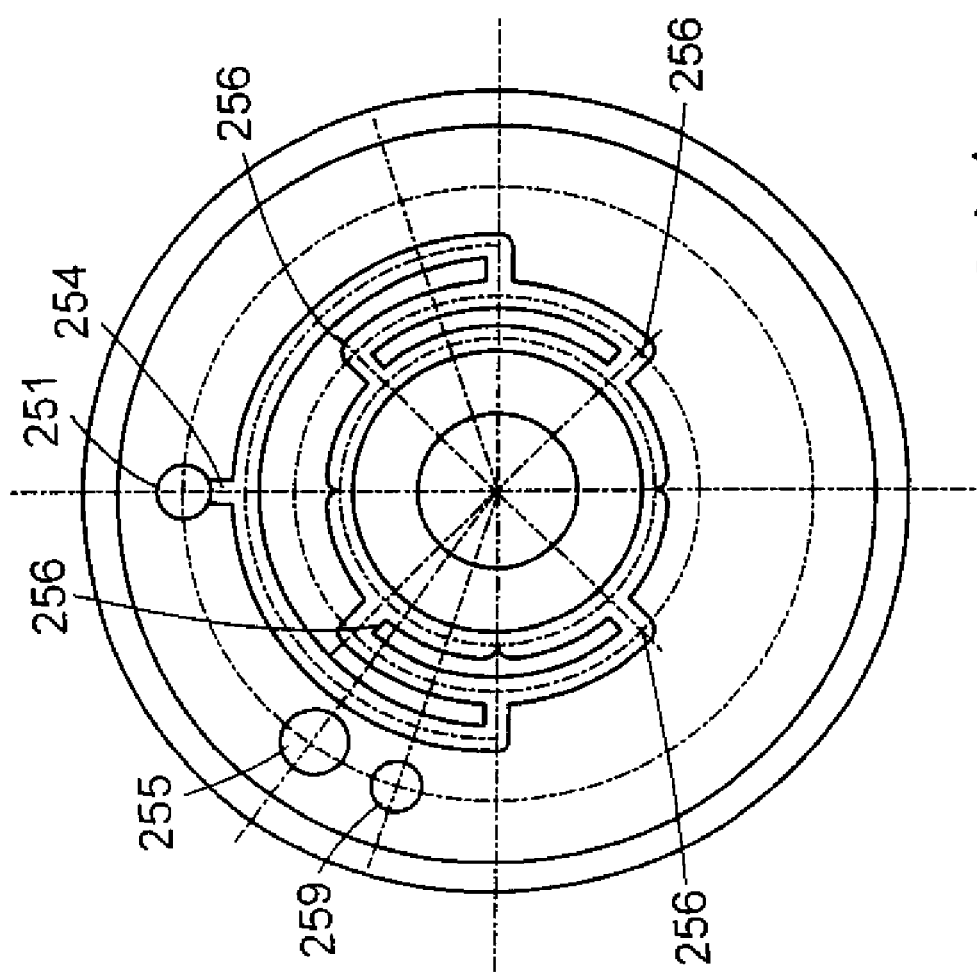
Figures 2, 9E:
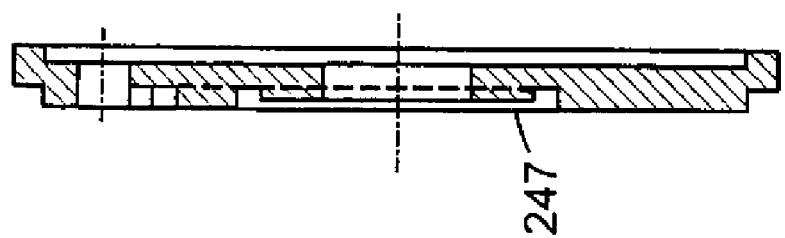
Figures 1, 9E:
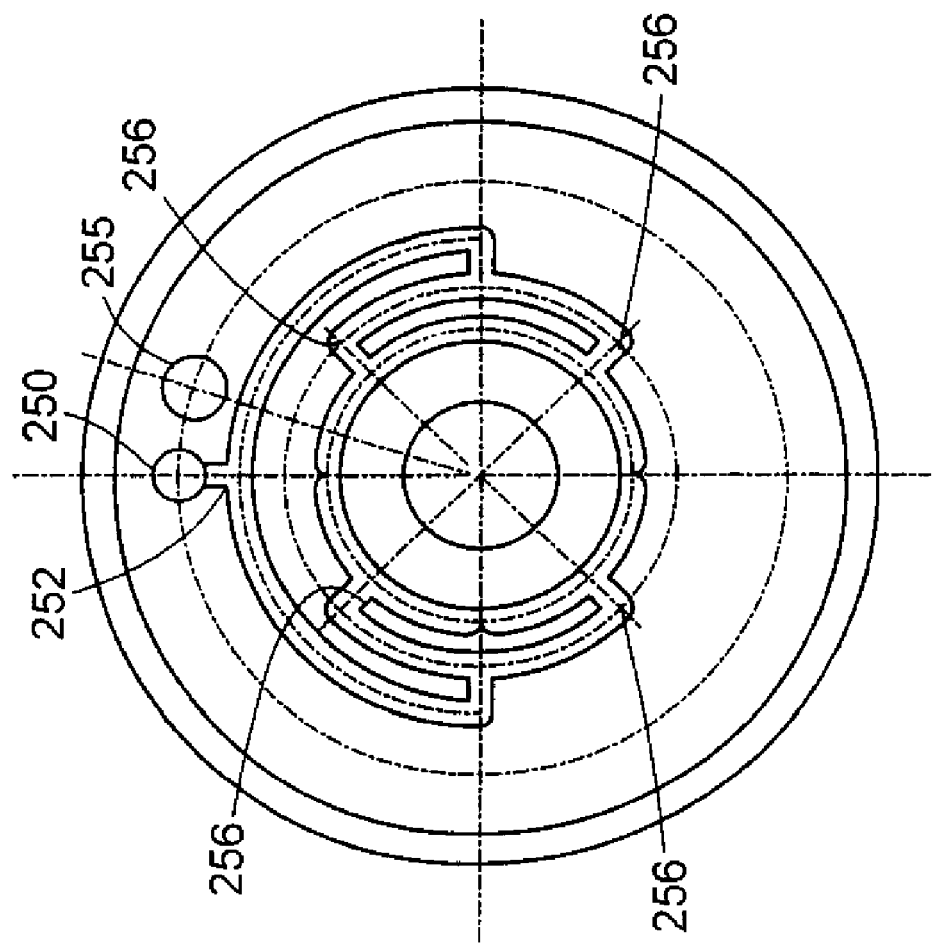
Figures 2, 9F:
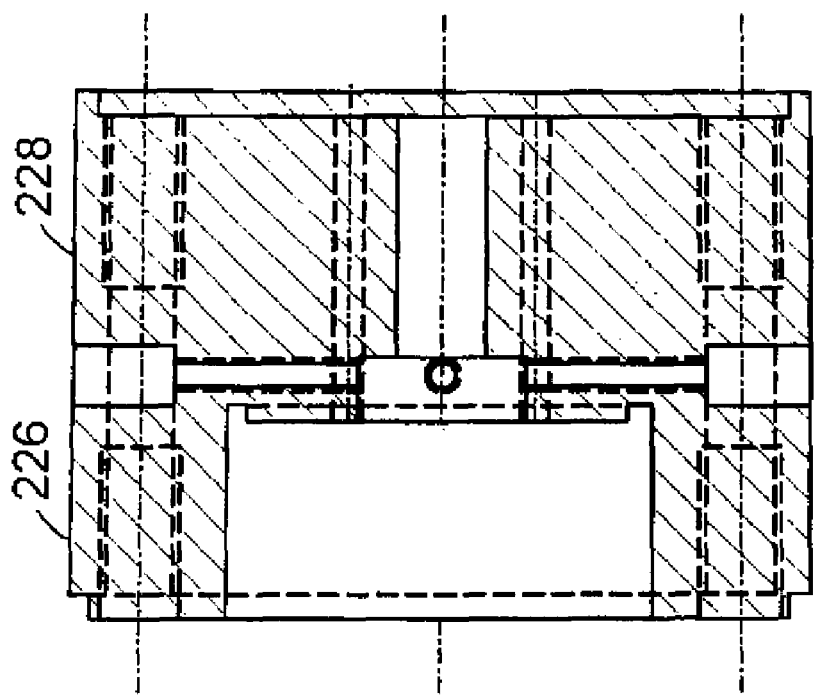
Figures 1, 9F:
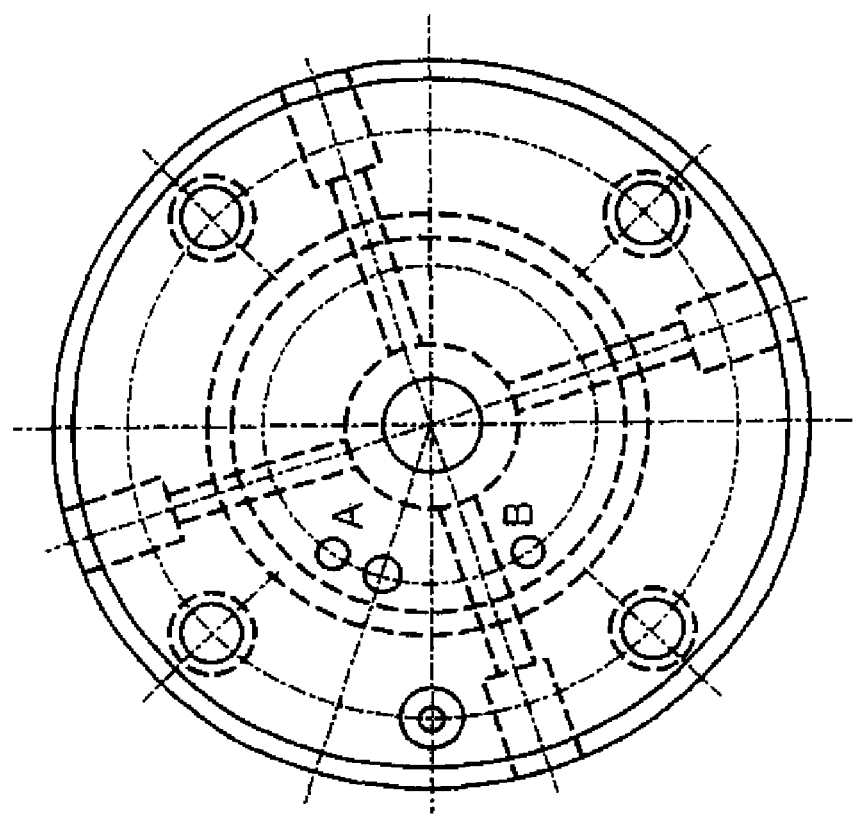
Figures 2, 9G:
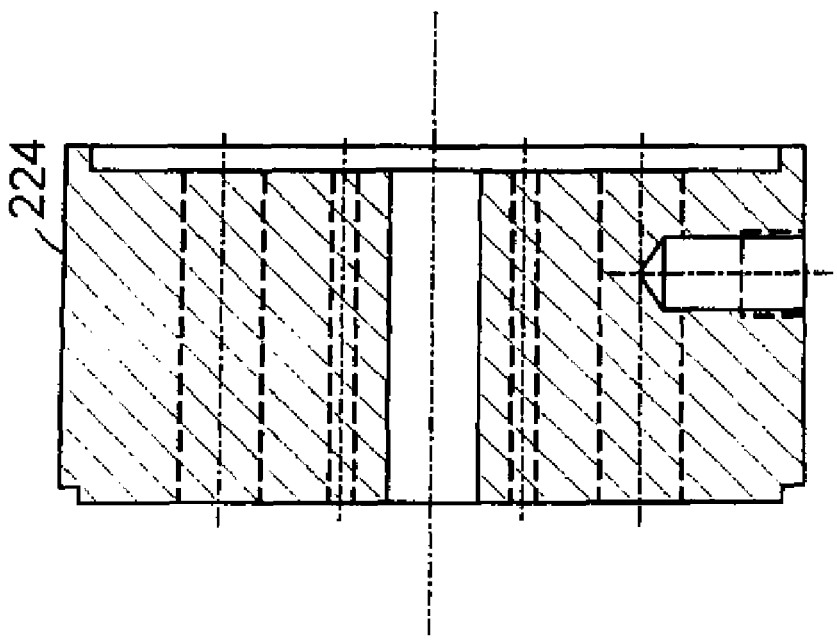
Figures 1, 9G:
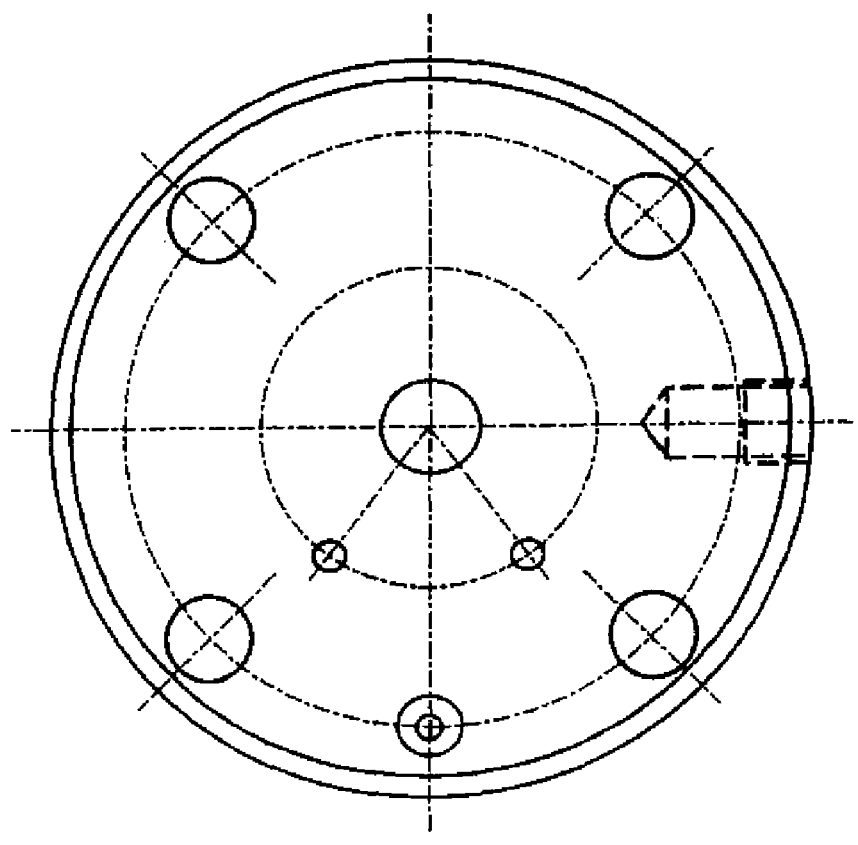
Figures 3, 9H:
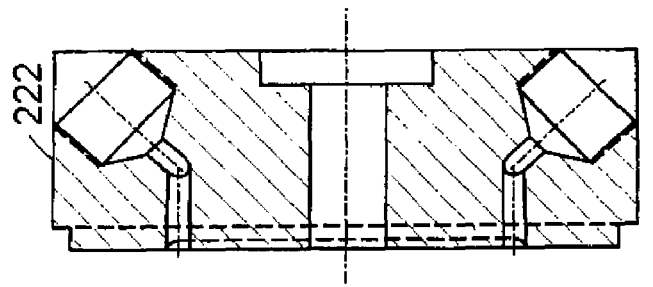
Figures 2, 9H:
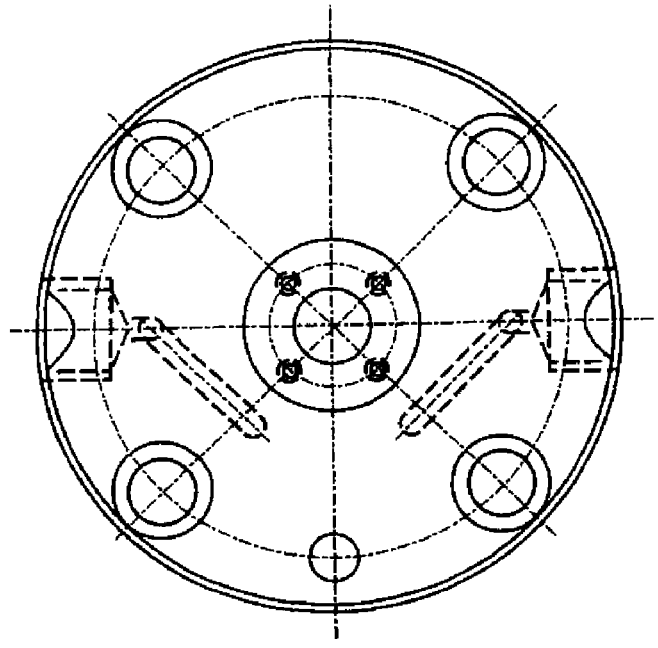
Figures 1, 9H:
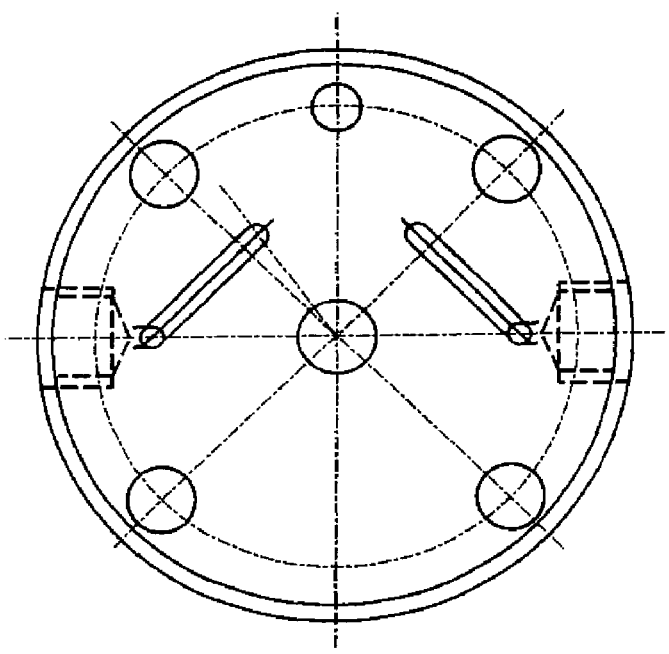
Figure 91:
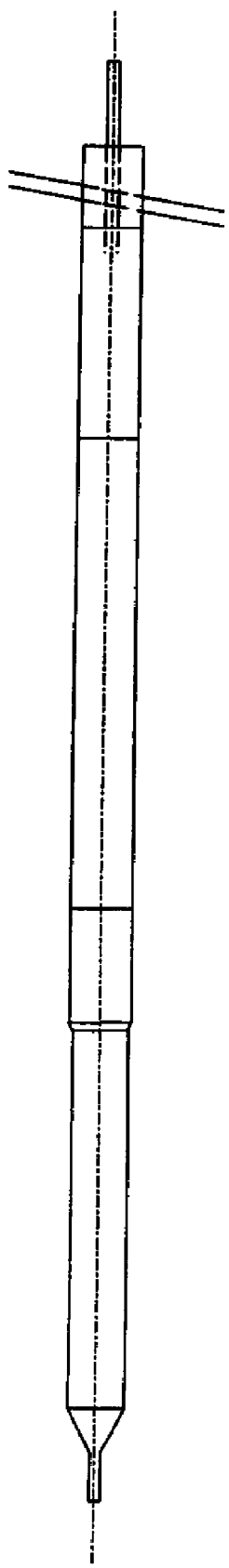
Figures 2, 9J:
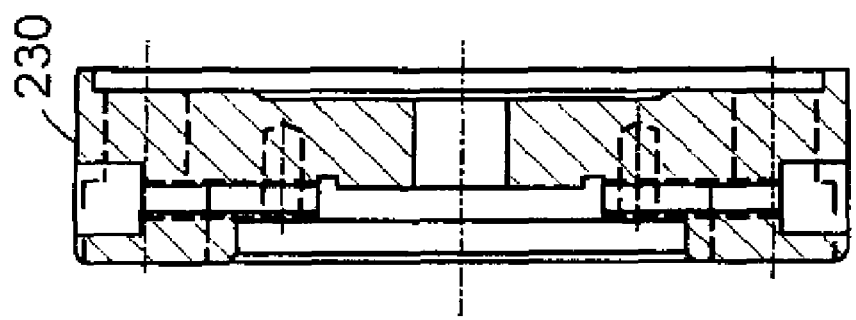
Figures 1, 9J:
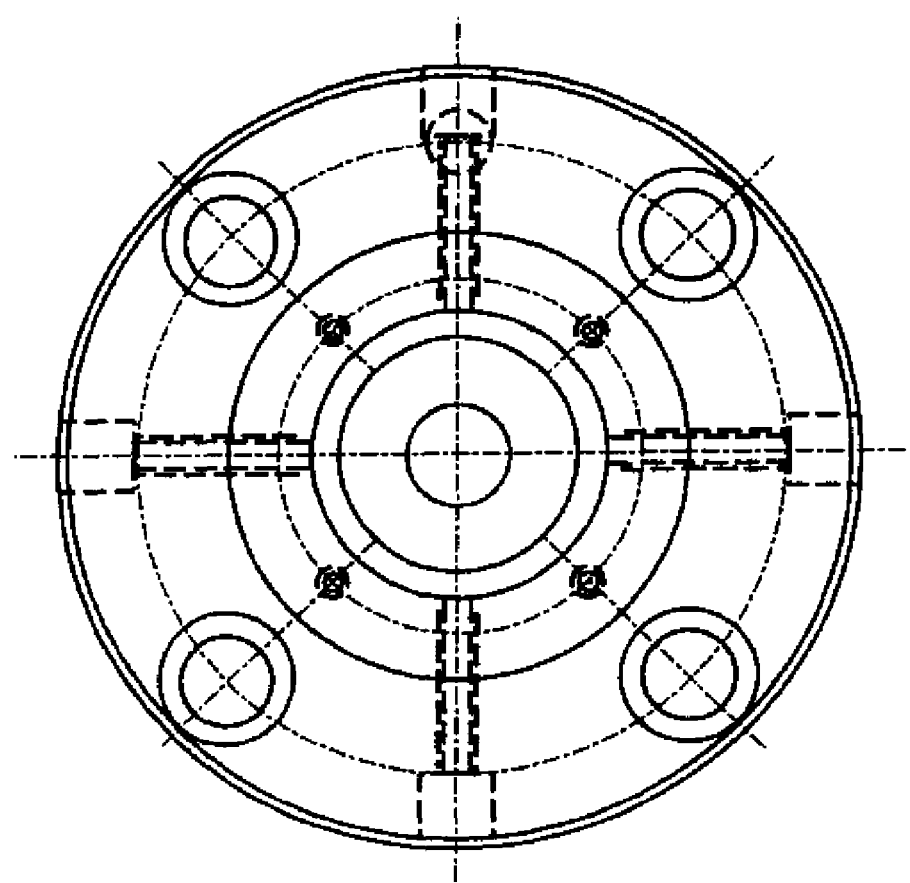
Figures 1, 2, 9K:
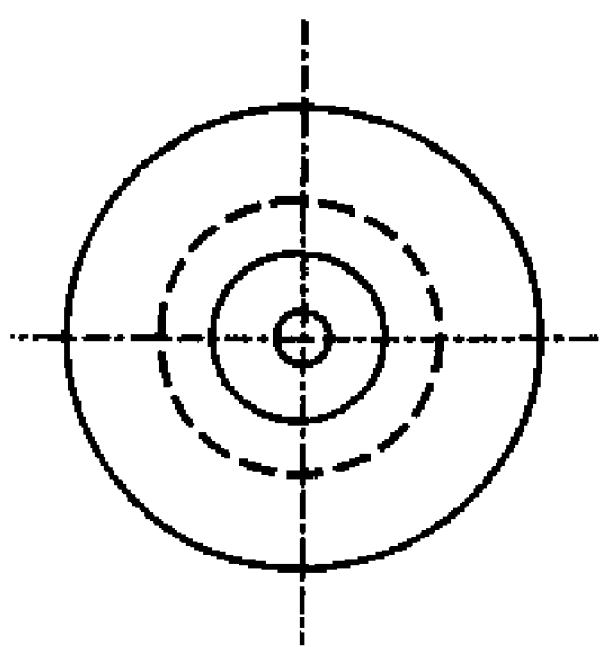

In certain embodiments, the thickness of one or more of the discs (e.g., at least two discs, at least three discs, at least four discs, at least five discs, at least six discs, at least seven discs, at least eight discs, at least nine discs, at least 10 discs, at least 11 discs, at least 12 discs, at least 13 discs, at least 20 discs, etc., each disc) can be less than about one inch (e.g., less than about 0.75 inch, less than about 0.5 inch, less than about 0.4 inch, less than about 0.3 inch, less than about 0.2 inch, less than about 0.15 inch, less than about 0.1 inch, less than about 0.05 inch) in the direction parallel to the flow of material (polymer) through the apparatus (e.g., in the direction L shown in FIG. 9).

In some embodiments, an apparatus has a 13 disc stack having a total thickness of less than about 13 inches (e.g., less than about 12 inches, less than about 11 inches, less than about 10 inches, less than about nine inches, less than about eight inches, less than about seven inches, less than about six inches, less than about 5.5 inches, less than about five inches, less than about 4.5 inches, less than about four inches, less than about 3.5 inches, less than about three inches, less than about 2.5 inches, less than about two inches, less than about 1.9 inches, less than about 1.8 inches) in the direction parallel to the flow of material (polymer) through the apparatus (e.g., in the direction L shown in FIG. 9).

In certain embodiments, an apparatus has a 20 disc stack having a total thickness of less than about 20 inches (e.g., less than about 19 inches, less than about 18 inches, less than about 17 inches, less than about 16 inches, less than about 15 inches, less than 14 inches, less than about 13 inches, less than about 12 inches, less than about 10 inches, less than about 9.5 inches, less than about nine inches, less than about 8.5 inches, less than about eight inches, less than about 7.5 inches, less than about seven inches, less than about 6.5 inches, less than about 6.4 inches, less than about 6.3 inches, less than about 6.2 inches, less than about 6.1 inches, less than about six inches) in the direction parallel to the flow of material (polymer) through the apparatus (e.g., in the direction L shown in FIG. 9).

FIG. 9 shows a cross-sectional view of an embodiment of an extrusion apparatus (a compact crosshead) 220 that can be used in the preparation of a 13-layer tube. The tubes may be formed by co-extruding a multi-layer tube having the desired sequence of layers. Compact crosshead 220 that includes a series of assembly sections 222, 224, 226, 228, 230 with a common bore into which is placed a spacing mandrel 232 that encompasses an air supply tube 234. Assembly sections 222, 224, 226 define inlets 236, 238 from separate extruders (not shown) which feed different polymers (in this example polymer A and polymer B) into the head and include passageways 240, 242 which direct the polymers to assembly section 228.

Assembly section 228 houses a series 244, in this example thirteen, extrusion discs. Each of the discs includes passageways for both polymers but an extrusion inlet and outlet for only one of the polymers. (An exception is the last disc which includes a passageway for only one polymer.) In this way, the polymer flow continues along the assembly but each polymer is added to the extrusion stream in the desired order. In this example, every other disc has an inlet and outlet for the first polymer and every other intervening disc has an inlet and outlet for the second polymer.

FIGS. 9a-9e show five different four channel disc designs that can be used together in crosshead 220. The inlets and outlets of the discs are formed as machined channels in the face of the discs. Polymer A flows through a passageway 250 and polymer B flows through a passageway 251. (An opening 255 for an alignment pin is provided for registration of the discs.) The outlets are formed by channels 256 that lead to gaps between adjacent discs. For example, the first disc 246 has an inlet 252 and an outlet 247 for the first polymer and passageway 251 for the second polymer but no inlet or outlet for the second polymer. The second disc 248 has an inlet 254 and an outlet 249 for the second polymer and a passageway 259 for the first polymer but no inlet or outlet for the first polymer. As a result, the first polymer will be deposited as the innermost layer, the second polymer as the next adjacent layer, the first polymer will be the third layer and so on. At the end of the thirteenth disc a thirteen layer extrusion in which alternate layers of different polymers is achieved. The thirteenth disc (FIG. 9e) is formed without passageway 51. The extrusion is sized to the desired diameter at the nozzle 250 on assembly section 230. The crosshead provides for substantial flexibility in a compact design by changing the discs or outlet configurations of the discs to obtain a desired sequence of layers. As illustrated in the mechanical drawings, the diameter of the central opening in the discs can vary to facilitate polymer delivery along the stream. In addition, the channels can be arranged to direct polymer(s) into the stream at different radial orientations in successive discs.

Figure 10:
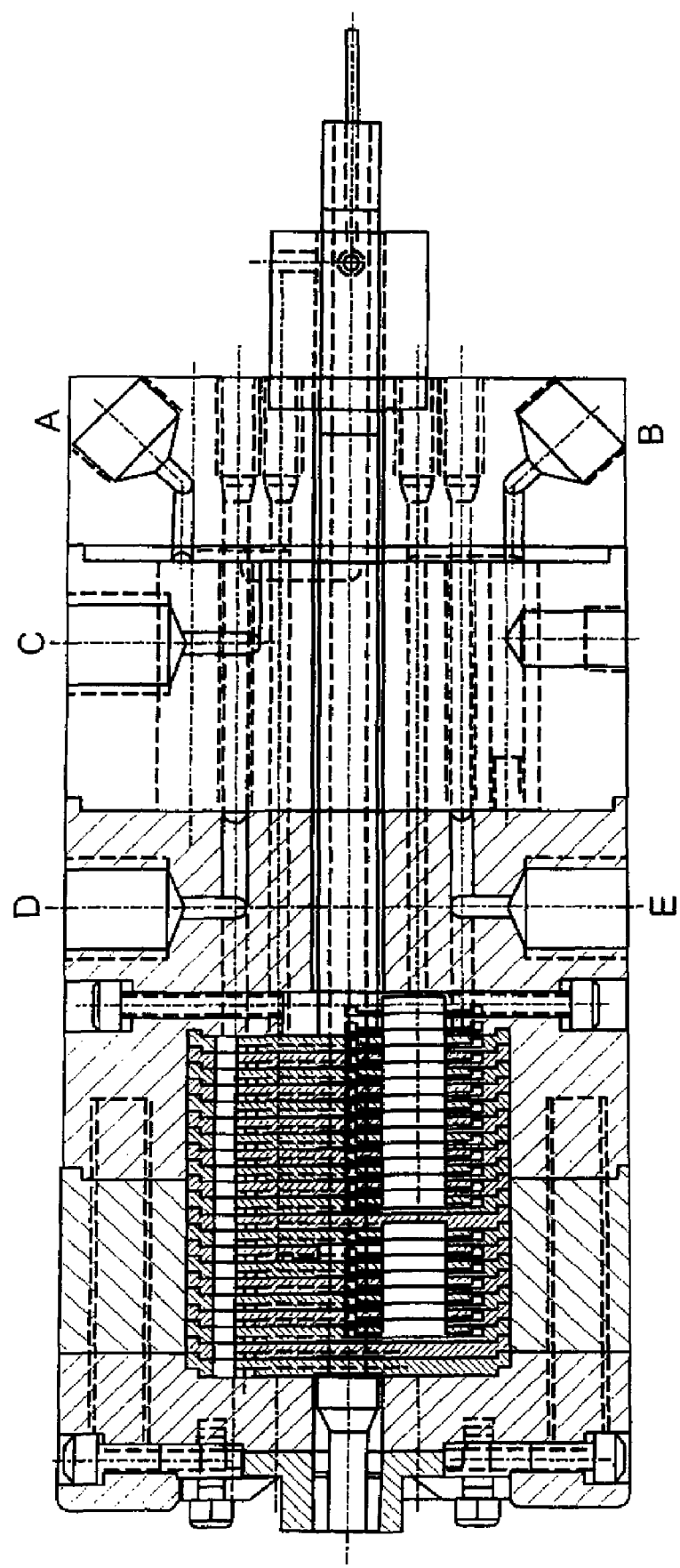
FIG. 10 is an assembly drawing of a crosshead arrangement according to an embodiment.
Figures 2, 11A:
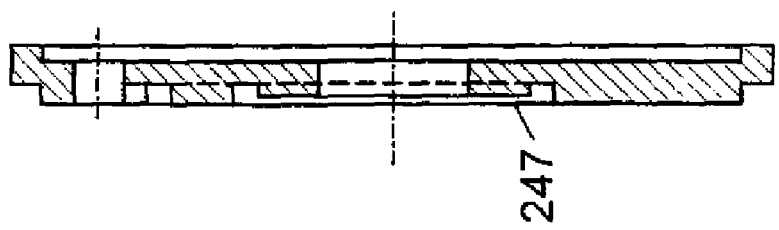
Figures 1, 11A:
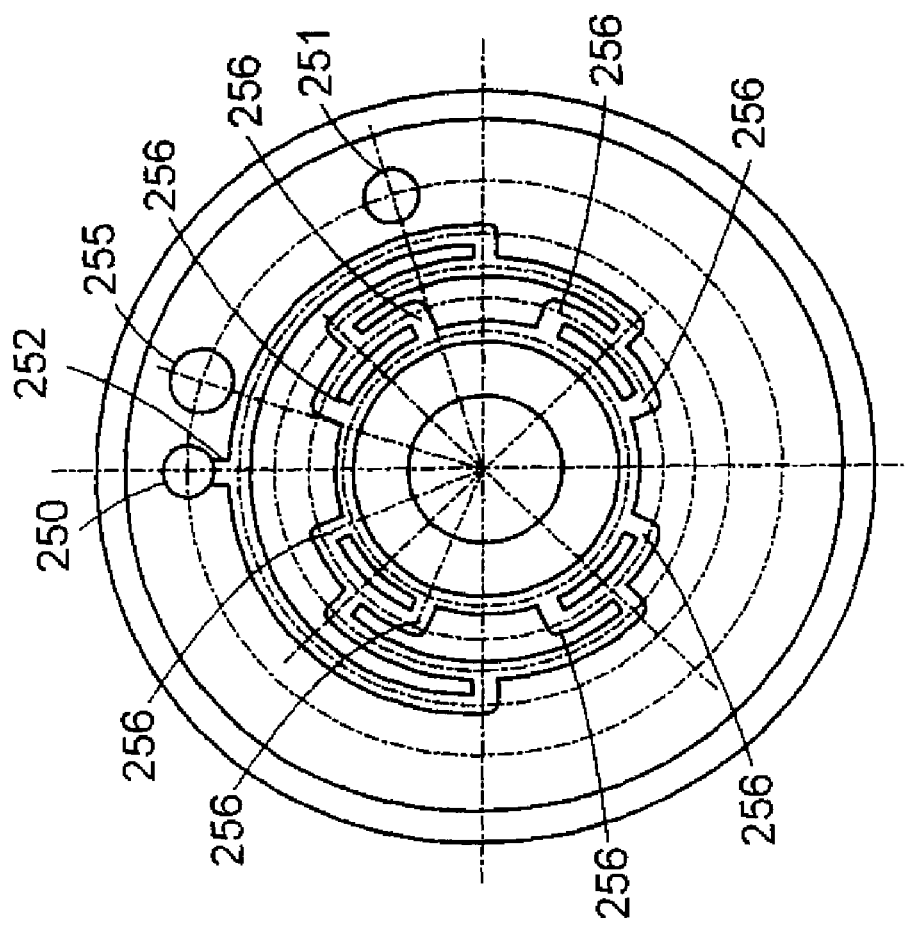
Figures 2, 11B:
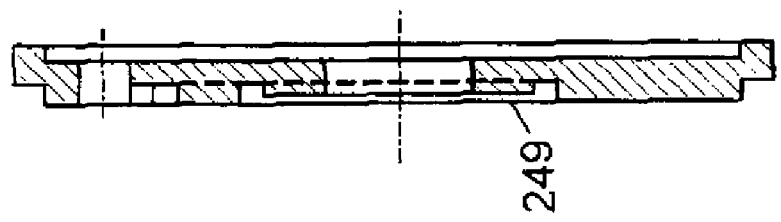
Figures 1, 11B:
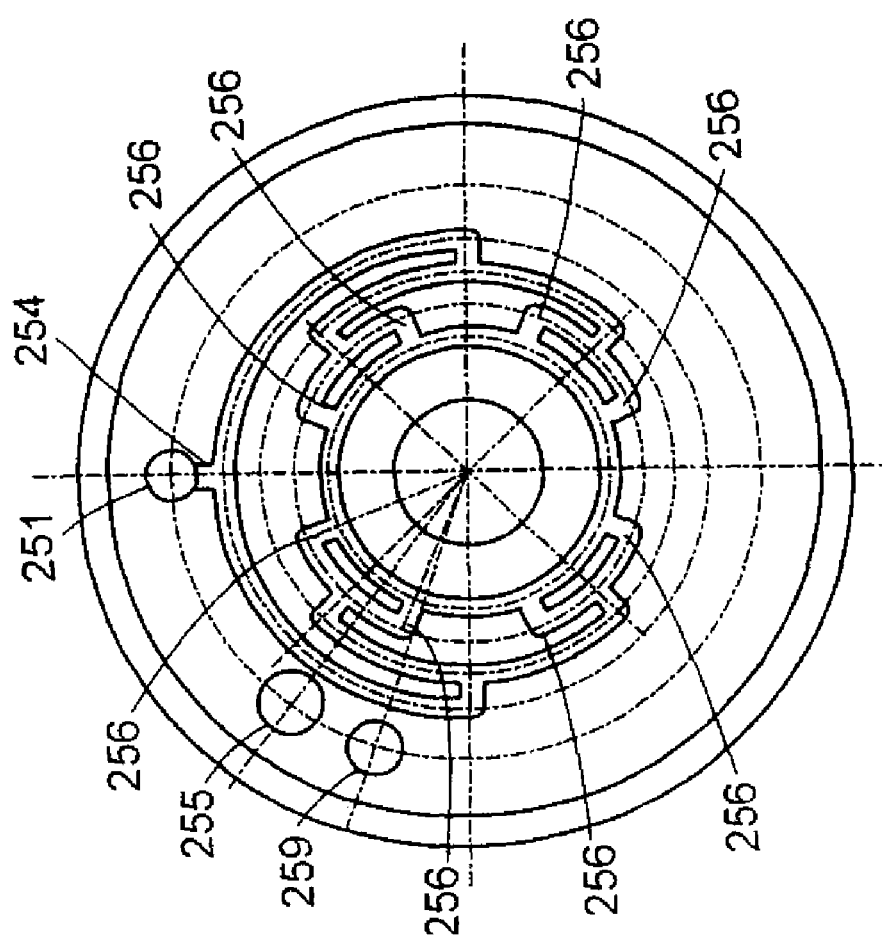
Figures 2, 11C:
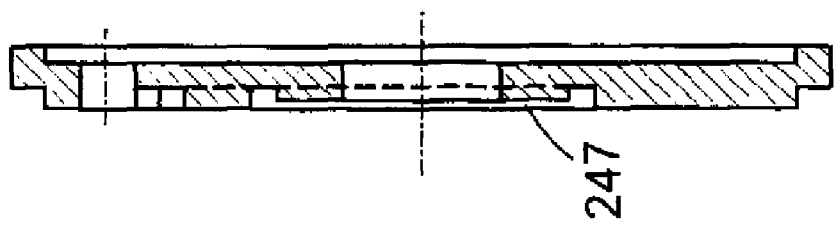
Figures 1, 11C:
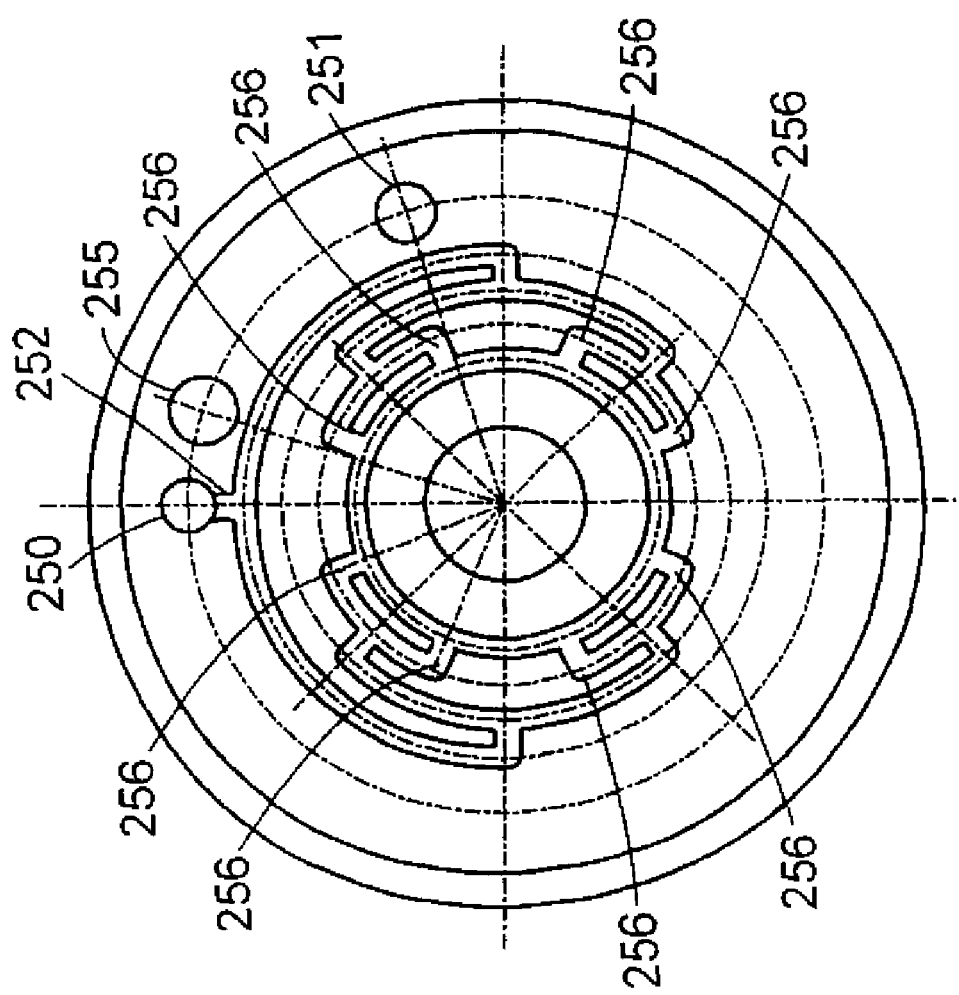
Figures 2, 11E:
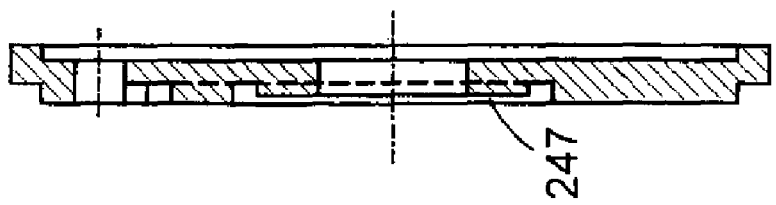
Figures 1, 11E:
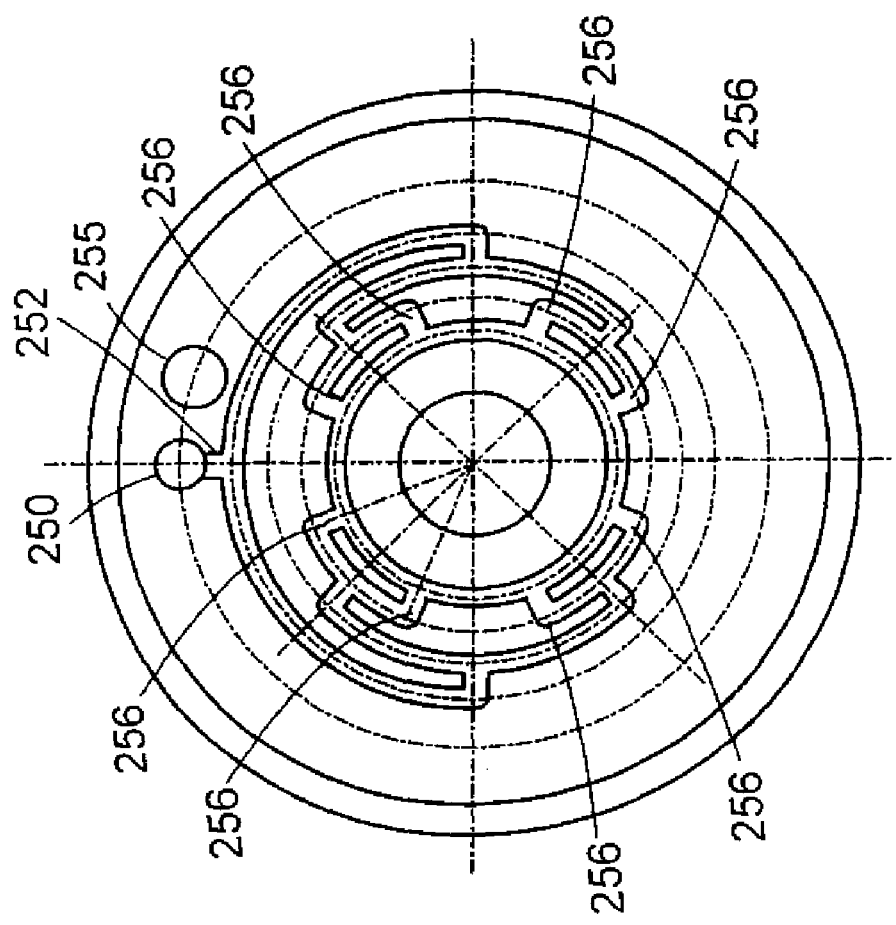

The number of layers can be varied from a single layer, two layers, three layers or more layers by controlling the number of discs. Referring as well to FIG. 10, a twenty-disc arrangement, the system can as well be adapted for co-extruding a greater number of polymers by replacing sections 224, 226, with sections that include additional extruder inlets and configuring the discs to include channels to accommodate the flow of the additional polymers. In the embodiment of FIG. 9, the assembly sections and the discs are formed of stainless steel and the system has an overall diameter, D, of about 3.5 inches and an overall length, L, of about 6.5 inches. The extruders may be one-inch Brabrender extruders (NJ). Some illustrative operating conditions, such as zone heating temperatures, polymer concentrations, feed rate, and line speed, are described in U.S. Ser. No. 09/798,749, entitled "Multilayer Medical Device" and filed on Mar. 2, 2001, hereby incorporated by reference in its entirety.

FIGS. 11a through 11e show five different eight channel disc designs that can be used together in crosshead 220 in a manner similar to that described above with respect to the four channel discs shown in FIGS. 9a through 9e. As shown in FIGS. 11a through 11e, however, these discs each have eight channels 256. This can result in the velocity of the polymer flow at outlet 247 being more uniform around the perimeter of outlet 247, thereby promoting circularity of individual layers in a tube, and/or increasing circularity of the interfaces between layers in a tube. The eight-channel pattern can be machined into the same size discs as the four-channel pattern so that the four and eight channel discs may be used with the same extrusion equipment. In certain embodiments, the width of the disc material between the channels generally constrains their size and location on the discs. For example, in some embodiments, discs machined from 440C stainless steel may maintain a minimum width between channels of about 0.035 inches without cracking under the pressure of the extruded polymer.

The thickness of individual layers can be controlled by controlling the feed rate or flow of the polymer(s). For example, to increase the thickness of a layer, the flow of material to that layer is increased. To decrease the thickness of the layer, the flow of material to that layer is decreased. The length of the transition portion(s) can be controlled by controlling the rate of change in the flow of the material. An abrupt flow change tends to produce to a relatively short transition portion, and a relatively gradual change in flow can produce a relatively long transition portion. Stopping the flow of material can cause a layer to terminate within the tube, e.g., layer 124 (FIG. 7). A preferred system for controlling the feed rate or flow of polymers, including melt pumps, and systems and methods for controlling the pumps, is described in WO 01/32398, entitled "Method and Apparatus for Extruding Catheter Tubing", hereby incorporated by reference in its entirety. Other methods include using servo-controlled valves, as described in Burlis et al., U.S. Pat. No. 3,752,617, hereby incorporated by reference.

OTHER EMBODIMENTS

Figure 12:
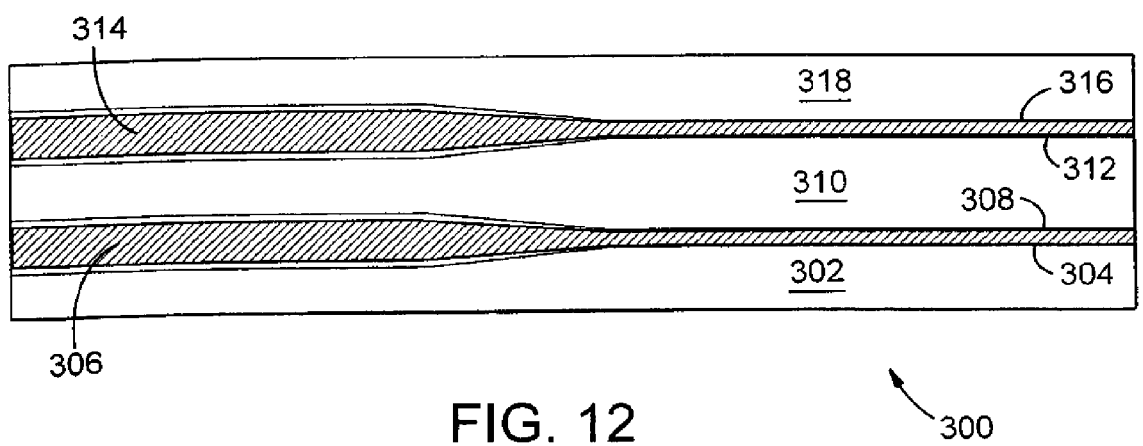
FIG. 12 is a cross-sectional view of an embodiment of a wall of medical device.

In other embodiments, a tube wall may include an adhesive layer between layers of other materials. Referring to FIG. 12, a tube wall 300 includes nine layers 302, 304, 306, 308, 310, 312, 314, 316, and 318. Layers 302, 310, and 318 are formed of a first material; layers 306 and 314 are formed of a second material; and layers 304, 308, 312, and 316 are formed of an adhesive. The adhesive can be used, e.g., when the first and second materials are immiscible. As shown, layers 304, 308, 312, and 316 substantially match layers 306 and 314, but in other embodiments, layers 304, 308, 312, and 316 can be formed in any configuration described above.

Layers 304, 308, 312, and 316 can be formed of any adhesive material appropriate for use in a medical device. The adhesive can be a polymer (e.g., a substantially pure polymer, or a blend of polymers). As an example, in certain embodiments, the adhesive is formed of an ethylene vinyl acetate polymer-containing material. As another example, in some embodiments, the adhesive is formed of an anhydride-modified polyolefin. An adhesive can be selected, for example, from the BYNEL® family of polymers (e.g., BYNEL® CXA Series, BYNEL® 1000 Series, BYNEL® 1123, BYNEL® 1124, BYNEL® 11E554, BYNEL® 11E573, BYNEL® CXA E-418), commercially available from E. I. DuPont de Nemours (Wilmington, Del.), the PLEXAR® family of polymers (e.g., PX360, PX360E, PX380, PX3227, PX3236, PX3277, PX5125, PX5327, PX206, PX209, PX2049, PX165, PX175, PX180, PX909, PX101, PX107A, PX108, PX114, PX1164), commercially available from Equistar Chemicals (Newark, N.J.), and/or the BLOX® family of polymers (e.g., BLOX® 200 Series), commercially available from the Dow Chemical Company (Midland, Mich.).

As an example, layers 302, 310, and 318 can be formed of any polyester-containing material (e.g., a substantially pure polyester, a blend containing at least one polyester) appropriate for use in a medical device. Such polymers include, for example, polyester homopolymers and/or copolymers (e.g., block copolymers) of polyesters. Examples of polyesters include PET polymers, PBT polymers and blends and combinations thereof, such as the SELAR® PT family of polymers (e.g., SELAR® PT 8307, SELAR® PT4274, SELAR® PTX280, DuPont (Wilmington, Del.)), the CLEARTUF® family of polymers (e.g., CLEARTUF® 8006, M&G Polymers (Apple Grove, W. Va.)), the TRAYTUF® family of polymers (e.g., TRAYTUF® 1006, Shell Chemical (Houston, Tex.), the MELINAR® family of polymers, DuPont, the CELANEX® family of polymers, Ticona (Summit, N.J.), the RITEFLEX® family of polymers, Ticona, the HYTREL® family of polymers (e.g., HYTREL® 5556, HYTREL® 7246, HYTREL® 4056), DuPont, and the ARNITEL® family of polymers (e.g., ARNITEL® EM630), DSM (Erionspilla, Ind.).

Layers 306 and 314 can be formed of any polyamide-containing material (e.g., a substantially pure polyamide, a blend containing at least one polyamide) appropriate for use in a medical device. Such polymers include, for example, polyamide homopolymers and/or copolymers (e.g., block copolymers) of polyamides. One type of polyamide includes the nylon family of polymers, including, for example, aliphatic nylons and aromatic nylons, such as, e.g., Nylon 11 (Atofina (Philadelphia, Pa.)), Nylon 6 (Honeywell (Morristown, N.J.)), Nylon 6/10 (BASF (Mount Olive, N.J.)), Nylon 6/12 (Ashley Polymers (Cranford, N.J.)), Nylon 12, Nylon MXD-6, the GRIVORY® family of polymers (EMS (Sumter, S.C.)), the GRILAMID® family of polymers (EMS), the VESTAMID® family of polymers (Daicel-Degussa Ltd), and the PEBAX® family of polymers (e.g., PEBAX® 5533, PEBAX® 2533, PEBAX® 7033, Atofina).

The tubes described above can be formed into a guide wire, e.g., a polymer guide wire. Methods of making a guide wire, including one having good torque transmission is described in U.S. Pat. No. 5,951,494, hereby incorporated by reference in its entirety.

EXAMPLE 1

The following example shows the results from simulations studying the effect of the number of layers and their radial placement on the stiffness of a tube. The layers in the samples discussed below alternate. The wall thickness remained constant for all samples. The calculations are based on uniformly distributed layers of equal thickness.

TABLE 1

| Sample | Material (Wt. Percent) | Layer | Stiffness (g-mm/deg) |
|---|---|---|---|
| A | PEBAX ® 7033 | Single | 0.545 |
| B | PEBAX ® 7033/7233 (50/50) | 2-layer, 7033 outer | 0.664 |

TABLE 1-continued

| Sample | Material (Wt. Percent) | Layer | Stiffness (g-mm/deg) |
|---|---|---|---|
| C | PEBAX ® 7033/7233 (35/65) | 2-layer, 7033 outer | 0.711 |
| D | PEBAX ® 7033/7233 (35/65) | 7-layer, 7033 outer | 0.723 |
| E | PEBAX ® 7033/7233 (35/65) | 13-layer, 7033 outer | 0.737 |
| F | PEBAX ® 7233/7033 (65/35) | 13-layer, 7233 outer | 0.739 |
| G | PEBAX ® 7233/7033 (50/50) | 2-layer, 7233 outer | 0.752 |
| H | PEBAX ® 7233/7033 (65/35) | 7-layer, 7233 outer | 0.761 |
| I | PEBAX ® 7233/7033 (65/35) | 2-layer, 7233 outer | 0.796 |
| J | PEBAX ® 7233 | Single | 0.867 |

Sample A is a tube formed of pure PEBAX® 7033, and Sample J is a tube formed of pure PEBAX® 7233, which is stiffer than PEBAX® 7033, as indicated by the higher stiffness (0.867 vs. 0.545 g-mm/deg).

Sample B is a two-layer tube, in which the outer layer is PEBAX® 7033 and the inner layer is PEBAX® 7233. The ratio of PEBAX® 7033 to PEBAX® 7233 is 50:50. The stiffness of Sample B is higher than the stiffness of Sample A because, compared to Sample A, there is more stiff material, i.e., PEBAX®) 7233 (a stiff material) has replaced PEBAX® 7033 (a more flexible material). Compared to Sample J, Sample B is less stiff because the stiff PEBAX® 7233 has been replaced by the more flexible PEBAX® 7033.

Sample C is a two-layer tube, in which the outer layer is PEBAX® 7033 and the inner layer is PEBAX® 7233. The ratio of PEBAX® 7033 to PEBAX® 7233 is 35:65. Compared to Sample B, Sample C is more stiff because Sample C has more stiff material —65% PEBAX® 7233 vs. 50% PEBAX® 7233.

Sample D is a seven-layer tube, in which the outer layer is PEBAX® 7033, and the ratio of PEBAX® 7033 to PEBAX® 7233 is 35:65. Compared to Sample C, Sample D is stiffer because more of the PEBAX® 7233 has been distributed to the outer surface of the tube. That is, whereas in Sample C, all of the PEBAX® 7233 was adjacent to the inner surface of the tube, in Sample D, some of the PEBAX® 7233 has been moved radially outward, thereby affecting the moment of inertia of the tube more.

Sample E is a thirteen-layer tube, in which the outer layer is PEBAX® 7033, and the ratio of PEBAX® 7033 to PEBAX® 7233 is 35:65. Compared to Sample D, Sample E is stiffer because more of the PEBAX® 7233 has been distributed to the outer surface of the tube.

Sample F is a thirteen-layer tube, in which the outer layer is PEBAX® 7233, the ratio PEBAX® 7233 to PEBAX® 7033 is 65:35. Compared to Sample E, Sample F is stiffer because the stiff material (PEBAX® 7233) is formed on the outer surface of the tube. The difference is less pronounced than when the stiff and flexible materials change positions in Samples C and I because of the larger number of layers.

Sample G is a two-layer tube in which the outer layer is PEBAX® 7233, the ratio PEBAX® 7233 to PEBAX® 7033 is 50:50. Compared to Sample B, Sample G is stiffer because the stiffer PEBAX® 7233 is formed on the outer surface of the tube.

Sample H is seven-layer tube in which the outer layer is PEBAX® 7233, the ratio PEBAX® 7233 to PEBAX® 7033 is 65:35. Compared to Sample F, Sample H is stiffer because more of the PEBAX® 7233 has been distributed to the outer surface of the tube. Compared to Sample D, Sample H is stiffer because the stiffer PEBAX® 7233 is formed on the outer surface of the tube.

Sample I is a two-layer tube in which the outer layer is PEBAX® 7233, the ratio PEBAX® 7233 to PEBAX® 7033 is 65:35. Compared to Sample C, Sample I is stiffer because the stiffer PEBAX® 7233 is formed on the outer surface of the tube. Compared to Samples F and H, Sample I is stiffer because more of the PEBAX® 7233 has been distributed, e.g., concentrated to the outer surface of the tube. However, compared to Sample J, Sample I is less stiff because some of the PEBAX® 7233 has been replaced by the more flexible PEBAX® 7033.

EXAMPLE 2

A nine-layer tube (0.022" O.D.×0.017" I.D.) having alternating layers of PEBAX® 7233 and PEBAX® 5533 (i.e., an ABABABABA construction where PEBAX® 5533 was the "A" layer and PEBAX® 7233 was the "B" layer) was made by the following procedures.

Two extruders (Brabender Prepcenters (Type D-51)) were used, each with ¾" barrels (05-09-N55). One extruder fed PEBAX® 7233 and the other extruded PEBAX® 5533. The temperatures (in Fahrenheit) were 80-345-365-385 for both extruders. For the PEBAX® 7233, the temperatures forward of the clamp were 395-395-395, and for the PEBAX® 5533, the temperatures forward of the clamp were 385-385-395.

Two pumps (Zenith, 0.16 cc/rev) were used. For the PEBAX® 7233 pump, the efficiency was 83.6%, and for the PEBAX® 5533, the efficiency was 88.3%. The efficiencies affect the pump settings to get a given amount of material. The inlet pressure for the pumps was about 1500 psi.

The extrusion head was the same as that described in U.S. application Ser. No. 09/798,749, with eight-channel disks. A LaserMike192 was used to gauge the O.D., and a Nikon toolscope with Quadrachek200 was used to visually examine the tubes. A puller (Model Tapertube 0.5, having an OLC servo-controlled air box, from RDN Manufacturing Co., Inc., Bloomingdale, Ill.) was used, and a water bath was set at 70° F.

The extrusion was based on distance down a part. That is, gearpump changes were based on movement of the tube, not, for example, based on time. For example, once two inches of tube has been extruded, the first melt/gear pump would go from no movement to 7.84 rpm. After 504 inches has been extruded, the same pump would go back to zero rpm. The cycle repeats itself. ,

TABLE 2

| Distance (in.) | Melt pump 1 (rpm) | Melt pump 2 (rpm) | AirVoltage (1 V = about 3 inches H$_2$O) |
|---|---|---|---|
| 0 | 0 | 7.42 | 4.95 |
| 0.5 | 0 | 0 | 4.95 |
| 2 | 7.84 | 0 | 4.95 |
| 378 | 7.84 | 0 | 4.5 |
| 380 | 7.84 | 0 | 5 |
| 504 | 7.84 | 0 | 5 |
| 504.5 | 0 | 0 | 5 |
| 505 | 0 | 7.42 | 5 |
| 649 | 0 | 7.42 | 5.8 |
| 919 | 0 | 7.42 | 5.45 |
| 920 | 0 | 7.42 | 5.1 |
| 999 | 0 | 7.42 | 4.95 |

A linear interpolation was used between consecutive points. The tube was about 83 feet long. In a 50-inch length, a transition was achieved from about 8% PEBAX® 7233, mainly in the inner layers, to about 55% PEBAX® 7233, mainly in the outer layers. The system took approximately two hours to achieve equilibrium so that the relative amounts of each material were substantially constant along the length of the piece.

All of the features disclosed herein may be combined in any combination. Each feature disclosed may be replaced by an alternative feature serving the same, equivalent, or similar purpose. Thus, unless expressly stated otherwise, each feature disclosed is only an example of a generic series of equivalent or similar features.

All publications, applications, and patents referred to in this application are herein incorporated by reference to the same extent as if each individual publication or patent was specifically and individually indicated to be incorporated by reference in their entirety.

Other embodiments are within the claims.

What is claimed is:

1. An elongate tubular member for use in a medical device, the elongate tubular member having a wall thickness and comprising:
   a first coextruded layer and a second coextruded layer, the first and the second layers comprising a first material; and
   a third coextruded layer comprising a second material having a different stiffness than the first material, where the third layer is disposed between the first and second layers,
   wherein the first, second and third layers vary in thickness radially along the member and wherein the wall thickness is constant along substantially the entire length of the member, and
   wherein the layers extend substantially the length of the member.

2. The member of claim 1, wherein the member includes first and second regions where the first, second and third layers each have a constant non-zero thickness along a length of the member and a third region disposed between the first and second regions where the first, second and third layers vary radially along a length of the member.

3. The member of claim 1, wherein the member includes first and second regions where the first, second and third layers each vary radially along a length of the catheter and a third region disposed between the first and second regions where the first, second and third layers each have a constant non-zero thickness along a length of the member.

4. The member of claim 1, wherein the member is stiffer at a proximal end than at a distal end.

5. The member of claim 1, wherein the first, second and third layers vary in thickness for substantially the entire length of the member.

6. The member of claim 1, further comprising a fourth layer that varies in thickness radially along the member.

7. An elongate tubular member for use in a medical device, the elongate tubular member having a wall thickness and comprising:
   a first coextruded layer and a second coextruded layer, the first and the second layers comprising a first material; and
   a third coextruded layer comprising a second material having a different stiffness than the first material, where the third layer is disposed between the first and second layers,
   wherein the first, second and third layers vary in thickness radially along the member and wherein the wall thickness is constant along substantially the entire length of the member, and
   wherein the member includes two first regions where each of the first regions extends along a length of the tube and a second region extending along a length of the tube and disposed between the first regions,
   wherein the configuration of the first and second regions is selected from the group consisting of
   (a) the first, second and third layers in the first regions each having a constant non-zero thickness and the first, second and third layers in the second region having thicknesses that vary constantly along a length of the member, and
   (b) the first, second and third layers in the first regions each having thicknesses that vary constantly along a length of the member and the first, second and third layers in the second region having a constant non-zero thickness.

8. The member of claim 7, wherein the layers extend substantially the length of the member.

9. The member of claim 7, wherein the member is stiffer at a proximal end than at a distal end.

10. The member of claim 7, further comprising a gradual transition between the first regions and the second region.

11. The member of claim 7, wherein the member has the same number of layers for substantially the entire length of the member.

12. The member of claim 7, wherein the number of layers in the member decreases distally.

13. The member of claim 7, further comprising a fourth layer that varies in thickness radially along the member.

14. An elongate tubular member for use in a medical device, the elongate tubular member having a wall thickness and comprising:
   a first coextruded layer and a second coextruded layer, the first and the second coextruded layers comprising a first material; and
   a third coextruded layer comprising a second material having a different stiffness than the first material, where the third coextruded layer is disposed between the first and second coextruded layers,
   wherein the first, second and third coextruded layers vary in thickness radially along the member, and
   wherein, at any given point along the member, the first layer has substantially the same thickness as the second layer.

15. The member of claim 14, wherein the layers extend substantially the length of the member.

16. The member of claim 14, wherein the member is stiffer at a proximal end than at a distal end.

17. The member of claim 14, wherein, at any given point along the member, the first layer has the same thickness as the second layer.

18. The member of claim 14, wherein the first, second and third layers vary in thickness for substantially the entire length of the member.

19. The member of claim 14, wherein the first, second and third layers vary in thickness only in a central region of the length of the member.

20. The member of claim 14, wherein the wall thickness is constant along substantially the entire length of the member.

* * * * *